US010782260B2

(12) United States Patent
Tamida et al.

(10) Patent No.: US 10,782,260 B2
(45) Date of Patent: Sep. 22, 2020

(54) ELECTROSTATIC CAPACITANCE DETECTION DEVICE AND POWER CONVERSION APPARATUS

(71) Applicant: Mitsubishi Electric Corporation, Chiyoda-ku (JP)

(72) Inventors: Taichiro Tamida, Chiyoda-ku (JP); Takahiro Inoue, Chiyoda-ku (JP); Takashi Hashimoto, Chiyoda-ku (JP); Akihiko Iwata, Chiyoda-ku (JP); Shuhei Koyama, Chiyoda-ku (JP); Takahiko Kobayashi, Chiyoda-ku (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 0 days.

(21) Appl. No.: 16/309,532

(22) PCT Filed: Jun. 8, 2017

(86) PCT No.: PCT/JP2017/021348
§ 371 (c)(1),
(2) Date: Dec. 13, 2018

(87) PCT Pub. No.: WO2018/042809
PCT Pub. Date: Mar. 8, 2018

(65) Prior Publication Data

US 2019/0227020 A1 Jul. 25, 2019

(30) Foreign Application Priority Data

Aug. 29, 2016 (JP) ................................ 2016-166499

(51) Int. Cl.
*H02P 27/08* (2006.01)
*G01N 27/22* (2006.01)
(Continued)

(52) U.S. Cl.
CPC ......... *G01N 27/226* (2013.01); *F25B 31/026* (2013.01); *G01F 23/266* (2013.01);
(Continued)

(58) Field of Classification Search
CPC ...... H02P 27/08; H02P 29/0088; H02P 29/68; H02M 2001/327; H02M 1/14; H02M 7/5387
See application file for complete search history.

(56) References Cited

U.S. PATENT DOCUMENTS 4,344,293 A * 8/1982 Fujiwara .............. B60H 1/3225 331/143
4,490,988 A * 1/1985 Vogel ....................... H02H 5/00 340/631

(Continued)

FOREIGN PATENT DOCUMENTS

JP 2-291484 A 12/1990
JP 2002-317785 A 10/2002

(Continued)

OTHER PUBLICATIONS

International Search Report dated Sep. 12, 2017 in PCT/JP2017/021348 filed Jun. 8, 2017.

*Primary Examiner* — Rina I Duda
(74) *Attorney, Agent, or Firm* — Xsensus LLP

(57) ABSTRACT

Provided is an electrostatic capacitance detection device including: an electrode pair including a pair of electrodes, the electrode pair being arranged inside a compressor configured to compress refrigerant; a capacitor being connected in series to the electrode pair; an inverter having one of power lines connected to one end of series-connected electrode pair and capacitor, and is configured to drive the compressor, the power lines being used for driving the compressor; and a voltage detecting unit configured to
(Continued)

measure a voltage between the pair of electrodes of the electrode pair.

14 Claims, 11 Drawing Sheets

(51) Int. Cl.

| | |
|---|---|
| ***G01R 27/26*** | (2006.01) |
| ***F25B 31/02*** | (2006.01) |
| ***G01F 23/26*** | (2006.01) |
| ***G01N 33/28*** | (2006.01) |
| ***H02M 7/5387*** | (2007.01) |

(52) U.S. Cl.
CPC ........... *G01N 27/22* (2013.01); *G01N 27/228* (2013.01); *G01N 33/2888* (2013.01); *G01R 27/26* (2013.01); *H02M 7/53871* (2013.01); *H02P 27/08* (2013.01); *G01F 23/26* (2013.01)

(56) References Cited

U.S. PATENT DOCUMENTS

| | | | | |
|---|---|---|---|---|
| 4,575,668 | A * | 3/1986 | Baker | H02M 7/53873<br>318/811 |
| 4,870,831 | A * | 10/1989 | Kitamoto | F25B 49/022<br>62/84 |
| 6,986,259 | B2 * | 1/2006 | Takegami | F25B 13/00<br>62/192 |
| 8,733,116 | B2 * | 5/2014 | Won | F04B 39/0207<br>62/193 |
| 9,137,933 | B2 * | 9/2015 | Koyama | F25B 31/006 |
| 9,276,516 | B2 * | 3/2016 | Harada | H02M 1/44 |
| 2016/0146523 | A1 | 5/2016 | Hatakeyama et al. | |

FOREIGN PATENT DOCUMENTS

| | | | |
|---|---|---|---|
| JP | 3550229 | B2 | 8/2004 |
| JP | 2015-1191 | A | 1/2015 |
| WO | WO 2014/188566 | A1 | 11/2014 |

* cited by examiner

ELECTROSTATIC CAPACITANCE DETECTION DEVICE AND POWER CONVERSION APPARATUS

TECHNICAL FIELD

The present invention relates to a device configured to mainly detect, as a value of an electrostatic capacitance, a state of a liquid in a device, for example, a state of oil inside a compressor used in an air-conditioning apparatus, a refrigerating machine, or other apparatus.

BACKGROUND ART

A compressor used in an air-conditioning apparatus or a refrigerating machine is configured to compress gas (refrigerant) for conversion of the gas to energy by moving a motor and other mechanical parts with electrical energy. Positive-displacement compression mechanisms configured to compress the gas include a scroll compression mechanism, a rotary compression mechanism, and other compression mechanisms, and every mechanism is formed of mechanical parts, which are combined with very fine lapping and are moved to compress the refrigerant. Therefore, oil (refrigerating machine oil) for lubrication is always required in a gap between the parts of a positive-displacement compressor. As a result, the refrigerating machine oil and the refrigerant necessarily coexist inside the compressor.

In respect of its mechanism, the compressor is entirely or partially a high-pressure vessel since it is configured to compress the refrigerant. The compressor generally has a structure in which a motor, scroll, or other positive-displacement compressor is arranged inside the high-pressure vessel. A predetermined amount of refrigerating machine oil is always stored inside the vessel, and the refrigerating machine oil circulates inside the compressor structure to maintain sound mechanical operation of a compression device portion in which lapping occurs with the compression of the refrigerant. In other words, normal circulation of the refrigerating machine oil inside the compressor significantly affects reliability of the compressor operation.

Meanwhile, the compressor is a device configured to compress the refrigerant, and hence the refrigerant circulates inside the compressor. The refrigerating machine oil and the refrigerant coexist, and may be mixed in some cases inside the compressor. The refrigerant passes through the positive-displacement compressor and is discharged from the compressor, and at the time of discharge, part of the refrigerating machine oil is also discharged simultaneously. As a result, in a refrigerant circuit of the air-conditioning apparatus, not only the refrigerant but also the refrigerating machine oil circulates. Therefore, the amount of refrigerating machine oil inside the compressor may be depleted in some cases, and a problem in mechanical soundness of the compressor may occur in some cases (oil depletion detection). Meanwhile, if the amount of refrigerating machine oil inside the compressor is too large and a liquid level of the oil that is increased to interfere with a rotating portion of the motor may become a factor that reduces efficiency of a rotating machine. Therefore, it is desired that the amount of refrigerating machine oil inside the compressor be appropriately managed (oil level detection).

Moreover, a state in which the refrigerant is dissolved in the refrigerating machine oil to some extent is established inside the compressor. When a dissolved amount of refrigerant in the refrigerating machine oil is too large, lubricity expected of the oil is impaired, and the soundness of the positive-displacement compressor cannot be maintained. Moreover, the oil in which the refrigerant is excessively dissolved has a risk that, when a temperature is increased, the refrigerant is suddenly evaporated and is abruptly reduced in amount. Therefore, it is also extremely important to know how much refrigerant is dissolved in the refrigerating machine oil for the operation of the compressor (refrigerant concentration detection). For example, Patent Literature 1 discloses a technology in which electrodes are provided at the bottom of a compressor to detect an electrostatic capacitance of the electrodes, to thereby measure a liquid level of the oil and a state the oil of being mixed with the refrigerant.

CITATION LIST

Patent Literature

Patent Literature 1: Japanese Unexamined Patent Application Publication No. Hei 02-291484

SUMMARY OF INVENTION

Technical Problem

However, since the compressor is also a pressure vessel, it is difficult to detect a state inside the compressor. In a case of a mechanism like that disclosed in Patent Literature 1 described above, the electrostatic capacitance between the electrodes is extremely minute at about several pF to about several tens of pF. Meanwhile, the motor rotates to generate electrical noise above the compressor. It has been extremely difficult to accurately measure the minute electrostatic capacitance from the noise.

The present invention has been made to solve the above-mentioned problem, and an object thereof is to provide an electrostatic capacitance detection device and a power conversion apparatus, which are capable of accurately detecting a state of liquid inside an apparatus even when the apparatus includes a motor or other electric motor.

Solution to Problem

According to one embodiment of the present invention, there is provided an electrostatic capacitance detection device, comprising: an electrode pair including a pair of electrodes, the electrode pair being arranged inside a compressor configured to compress refrigerant; a capacitor being connected in series to the electrode pair; an inverter having a first power line connected to one end of a measurement target portion, and being configured to drive the compressor, the first power line being one of power lines for driving the compressor, the measurement target portion being formed by connecting the electrode pair and the capacitor in series to each other; and a voltage detecting unit configured to measure a voltage between the pair of electrodes of the electrode pair.

According to another embodiment of the present invention, there is provided an electrostatic capacitance detection device, comprising: an electrode pair including a pair of electrodes, the electrode pair being included in a liquid container; a capacitor connected in series to the electrode pair; an inverter having a power line connected to one end of series-connected electrode pair and capacitor, the power line being used for driving a device; a liquid, which is stored in the liquid container, and is to be used by the device driven by the inverter; and a voltage detecting unit configured to measure a voltage between the electrode pair.

According to still another embodiment of the present invention, there is provided a power conversion apparatus, comprising: an electrode pair; a capacitor connected in series to the electrode pair; a voltage detecting unit configured to detect a voltage between electrodes of the electrode pair; a compressor, in which the electrode pair is placed; and an inverter, which has one of power lines connected to one end of series-connected electrode pair and capacitor, and is configured to drive the compressor.

Advantageous Effects of Invention

According to the electrostatic capacitance detection device and the power conversion apparatus of the embodiments of the present invention, an AC voltage of inverter power lines can be applied to the electrode pair inside the liquid container by the capacitor. As a result, the electrostatic capacitance detection device and the power conversion apparatus detect an electrostatic capacitance formed between the electrode pair, and hence can perform accurate detection with a simple configuration without being affected by noise of the inverter.

DESCRIPTION OF EMBODIMENTS

Embodiment 1

Figure 1:
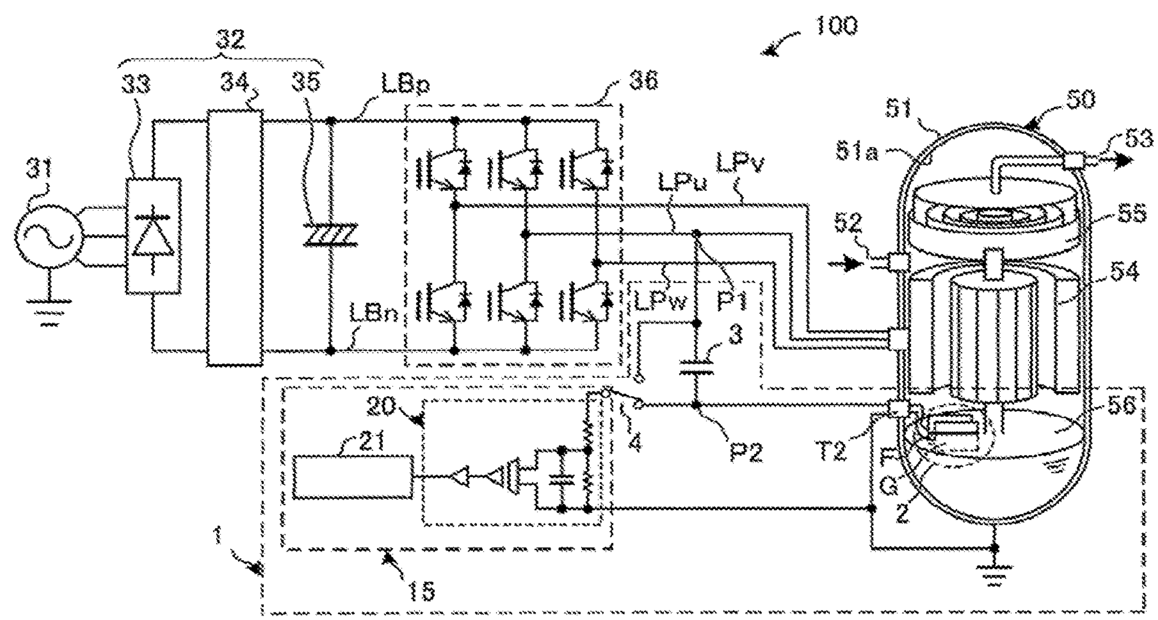
FIG. 1 is a diagram illustrating an installation configuration of an electrostatic capacitance detection device and a power conversion apparatus according to Embodiment 1 of the present invention.

FIG. 1 is a diagram illustrating an installation configuration of an electrostatic capacitance detection device and a power conversion apparatus according to Embodiment 1 of the present invention. In FIG. 1, a compressor 50 as an example of a load device, an inverter circuit configured to drive the compressor 50, and a detecting circuit portion of an electrostatic capacitance detection device 1 according to the present invention are illustrated, and those components form a power conversion apparatus 100.

The inverter circuit generally receives power from a single-phase or three-phase AC power source 31, and a DC voltage is generated through a converter circuit 32 including a rectifier circuit 33, a booster circuit 34, a smoothing capacitor 35, and other components. The rectifier circuit 33 is an AC-DC converter configured to rectify an AC voltage of the three-phase AC power source 31, and is formed of a three-phase full-wave rectifier obtained by bridge-connecting six diodes, for example. The rectifier circuit 33 outputs the rectified voltage to the booster circuit 34. The booster circuit 34 is a DC-DC converter configured to perform transformation to any voltage, and is formed of a boost chopper circuit, for example. The booster circuit 34 is configured to transform the voltage rectified by the rectifier circuit 33 and output the transformed voltage. The booster circuit 34 may be omitted depending on a target output. The smoothing capacitor 35 is formed of an electrolytic capacitor, for example, and is configured to smooth the output voltage that is output from the booster circuit 34.

The DC voltage (hereinafter referred to as "bus voltage") generated by the converter circuit 32 is converted into an alternating current by an inverter 36, and is applied to a motor 54 in the compressor 50. A line on a positive side and a line on a negative side of the DC voltage are referred to as a "P-bus LBp" and an "N-bus LBn", respectively. Cables of output lines of the inverter 36, that is, input lines of the compressor are referred to as "power lines LPu, LPv, and LPw". The inverter 36 is formed of a plurality of switching elements. As the switching elements, IGBT (insulated gate bipolar transistor) or MOSFET (metal-oxide-semiconductor-field-effect-transistor) elements or other elements are used, for example.

The compressor 50 is mainly formed of the motor 54 and a positive-displacement compressor 55, which is driven to rotate by the motor 54. In FIG. 1, a scroll compressor is illustrated as the positive-displacement compressor 55. Another type of compressor, for example, a rotary or reciprocating compressor, may be used instead. The compressor 50 is configured to suck refrigerant from an intake port 52, compress the sucked refrigerant with the positive-displacement compressor 55, and discharge the compressed refrigerant from a discharge port 53. The motor 54 is formed of a stator fixed to a shell housing 51 of the compressor 50 and a rotor at the center. In a portion below the rotor, there is an oil intake port, from which refrigerating machine oil 56 is sucked to be circulated through the positive-displacement compressor 55 and other parts of the compressor 50.

When the compressor 50 is vertical as in FIG. 1, the refrigerating machine oil 56 is accumulated in a lower portion of the compressor, and the oil is sucked from the oil intake port to circulate inside the compressor 50. A position of an oil level of the refrigerating machine oil 56 is important in managing the amount of oil. A vessel in which liquid as a detection target is stored is referred to as a "liquid container", and in Embodiment 1, the shell housing 51 corresponds to the liquid container.

An electrode pair 2 is arranged such that it is immersed in the refrigerating machine oil 56. The electrode pair 2 is intended to measure an electrostatic capacitance between the electrodes, and hence two metal plates arranged in parallel to each other is assumed. The two metal plates may have any shape in principle as long as the metal plates do not interfere with the compressor operation. The two electrodes are hereinafter referred to as an "electrode F" and an "electrode G".

A potential of the electrode F is extracted to the outside through a cable and a glass terminal T2. A measuring capacitor 3 is provided between the terminal extracted from the electrode F and a power line. Here, a general three-phase motor has three power lines (LPu, LPv, and LPw), and the power line may be any one (for example, LPu) of the three power lines. Meanwhile, the electrode G is connected to a ground potential. The shell housing 51 of the compressor 50 is generally grounded, and hence the electrode G is connected to the shell housing 51 of the compressor 50, for example. A potential of the electrode G is extracted to the outside by the glass terminal T2 and then grounded in FIG. 1, but may be connected inside the compressor 50. In that case, only the glass terminal for the F electrode is required, and one glass terminal becomes unnecessary.

In this configuration, a voltage between the electrode F and the shell housing 51 of the compressor 50, that is, the ground potential is input to a voltage measuring circuit. In FIG. 1, a voltage dividing circuit 22 configured to divide a measured voltage to a low voltage suited for the detection, and an insulation amplifier 24 configured to convert a potential of a measuring system, as primary steps, are illustrated.

Moreover, in the circuit of FIG. 1, a relay 4 is provided such that the potential of the electrode F and a potential of the power line LPu may be switched as a measurement target. This circuit is intended to measure the electrostatic capacitance between the electrode F and the electrode G. A measurement principle is described below.

First, operation of the inverter 36 is described. When the motor 54 is driven by the inverter 36, it is desired that an electric current that is as close to a sine wave as possible be allowed to flow through the motor 54. However, the inverter 36 turns the voltage ON/OFF with IGBT or other switching elements, and hence in the case of an element configuration as that of FIG. 1, for example, only a potential of one of the P-bus LBp and the N-bus LBn can be output. Meanwhile, the inverter 36 can perform switching at a frequency (for example, several kHz) that is much higher than a frequency (for example, 100 kHz) required for the motor 54. Therefore, the switching of the inverter 36 is repeated at a fast rate to change its pulse width, to thereby obtain an output close to a sine wave. This is called "PWM (pulse width modulation) control". The inverter 36 is controlled by an inverter control unit (not shown).

Figure 2:
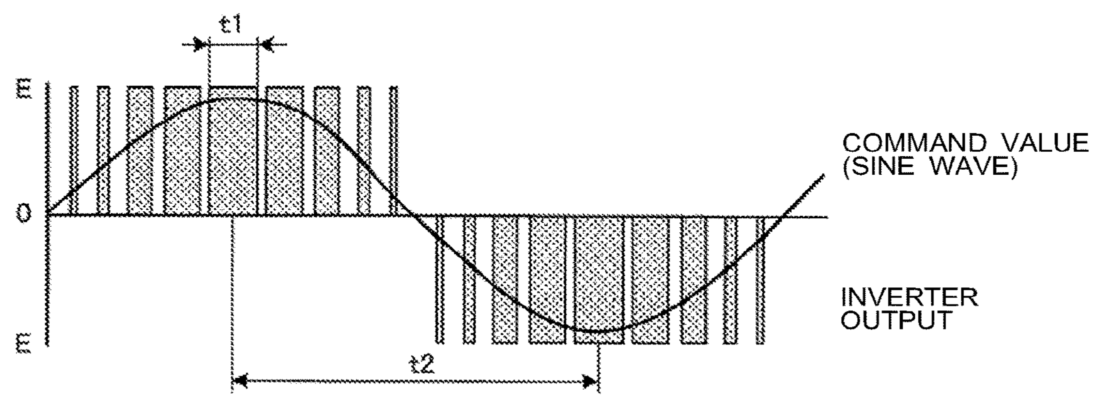
FIG. 2 is a graph showing PWM operation of an inverter.

FIG. 2 is a graph showing PWM operation of the inverter. In FIG. 2, how PWM control is performed is illustrated. It is desired to output a voltage waveform of the sine wave (command value), but such a voltage waveform cannot be output. Therefore, a voltage is output while changing a fine pulse width as shown in FIG. 2. With the voltage waveform, an electric current close to the sine wave is allowed to flow. In other words, the electric current having the sine wave flows through the motor 54, but the voltage of the inverter 36 is a series of high-frequency pulses.

Figure 3:
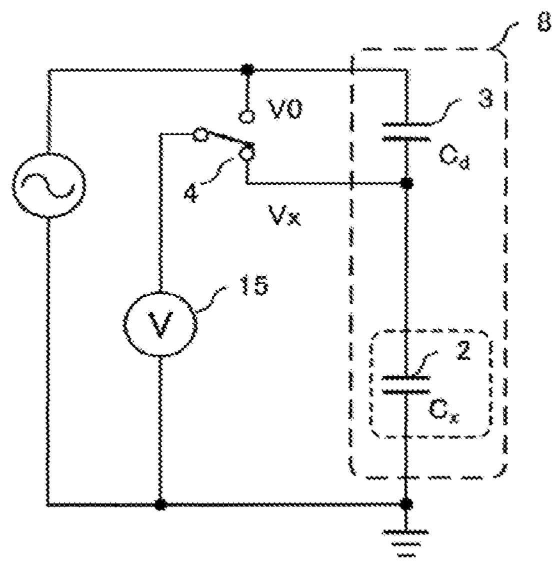
FIG. 3 is a diagram illustrating an equivalent circuit as a detection principle in Embodiment 1 of the present invention.

Next, the principle of measuring the electrostatic capacitance is described. FIG. 3 is a diagram illustrating an equivalent circuit as a detection principle in Embodiment 1 of the present invention. Cx is the electrostatic capacitance, that is, the measurement target formed by the electrode F and the electrode G, and Cd is an electrostatic capacitance of the measuring capacitor 3 provided between the electrode F and the inverter power line. The electrode G is connected to the shell housing 51, that is, the ground. The relay 4 performs switching between V0 and Vx, which is measured by a voltage measurement device 15.

The AC power source on the left indicates a fluctuation in potential of the inverter power lines. As described with reference to FIG. 2, the output voltage of the inverter 36 fluctuates at a high frequency through the PWM control. This high-frequency fluctuation component is applied to both ends of the measuring capacitor 3 and the electrode pair 2 connected in series. In other words, the AC voltage is applied to both ends of the measuring capacitor 3 and the electrode pair 2 connected in series and is divided by the measuring capacitor 3. The series-connected measuring capacitor 3 and electrode pair 2 is hereinafter referred to as a "measurement target portion 8" (see FIG. 3). At this time, when values (for example, amplitudes of the alternating current) of the voltage V0 before being divided and the voltage Vx after being divided are determined, a value of Cx can be calculated based on the following equation.

$$C_x = \frac{V_0 - V_x}{V_x} C_d \tag{1}$$

Actually, the measured electrostatic capacitance of the electrode pair 2 includes, in parallel, a considerable floating capacitance Cs. In this case, accurately, Cx+Cs in the left side of the expression (1) is measured. The floating capacitance Cs is caused by the structure of the device, and hence when a value of the floating capacitance Cs is evaluated in advance, the value of the electrostatic capacitance Cx of the electrode pair 2 can be determined based on the expression (1).

As described above, in Embodiment 1, the electrostatic capacitance detection device 1 includes the electrode pair 2, the measuring capacitor 3, a voltage detecting unit 21 configured to detect the voltage between the electrodes of the electrode pair 2, the compressor 50, in which the electrode pair 2 is installed, and the inverter 36 configured to drive the compressor 50. Then, to a power line (for example, power line LPu) of the inverter 36 configured to drive the compressor 50, one end of the measurement target portion 8 is connected. As a result, the electrostatic capacitance detection device 1 can detect the electrostatic capacitance formed between the electrode pair 2 by applying, with the measuring capacitor 3, the AC voltage of the inverter power lines to the electrode pair 2 inside the compressor 50.

Moreover, in the electrostatic capacitance detection device 1, the electrode pair 2 may be provided in a liquid container other than the compressor 50. As a result, the electrostatic capacitance detection device 1 can detect the electrostatic capacitance formed between the electrode pair 2 by applying, with the measuring capacitor 3, the AC voltage of the inverter power lines to the electrode pair 2 inside the liquid container. For example, the state (whether the oil is present or not, or is diluted with a liquid solvent) of liquid between the electrode pair 2 is detected.

Moreover, the electrostatic capacitance detection device 1 includes the voltage detecting unit 21, which is configured to detect the voltage between both ends of the measurement target portion 8, to detect the electrostatic capacitance of the electrode pair 2 based on the voltage between the electrodes of the electrode pair 2 and the voltage between both ends of the measurement target portion 8. As a result, the electrostatic capacitance detection device 1 can detect the electrostatic capacitance formed between the electrode pair 2 using the expression (1) described above based on the two detected voltage values.

Moreover, the other end of the measurement target portion 8 is grounded. As a result, when one of the electrodes is grounded, an electric current is allowed to flow to the ground from the power lines through the measuring capacitor 3 and the electrode pair 2, and the electrostatic capacitance between the electrodes can be detected based on the electric current thus generated.

Moreover, the inverter 36 is PWM-controlled. As a result, the high-frequency component appears on the power lines. This high-frequency component is suited for the measurement of the electrostatic capacitance.

Moreover, the electrostatic capacitance detection device 1 includes a switching mechanism (for example, relay 4) configured to switch a detection target of the voltage detecting unit 21 between the voltage Vx between the electrodes of the electrode pair 2 and the voltage V0 between both ends of the measurement target portion 8. The potential of the electrode F and the potential of the power lines are required for the measurement of the electrostatic capacitance, and hence the relay 4 is provided such that both potentials can be measured with one voltage detecting unit 21.

In Embodiment 1, the electrostatic capacitance detection device 1 has been described as a device configured to detect the state of the oil, the refrigerant, or a liquid mixture of the oil and the refrigerant inside the compressor 50, but the detection target is not limited thereto. For example, the electrostatic capacitance detection device 1 is also applicable to a receiver tank or an accumulator included in an air-conditioning apparatus driven by an inverter. Moreover, the electrostatic capacitance detection device 1 can perform liquid level detection when applied to an oil tank or other liquid container used in an apparatus driven by an inverter. Moreover, when the detection target is a liquid mixture, the electrostatic capacitance detection device 1 can also detect a concentration.

Embodiment 2

Figure 4:
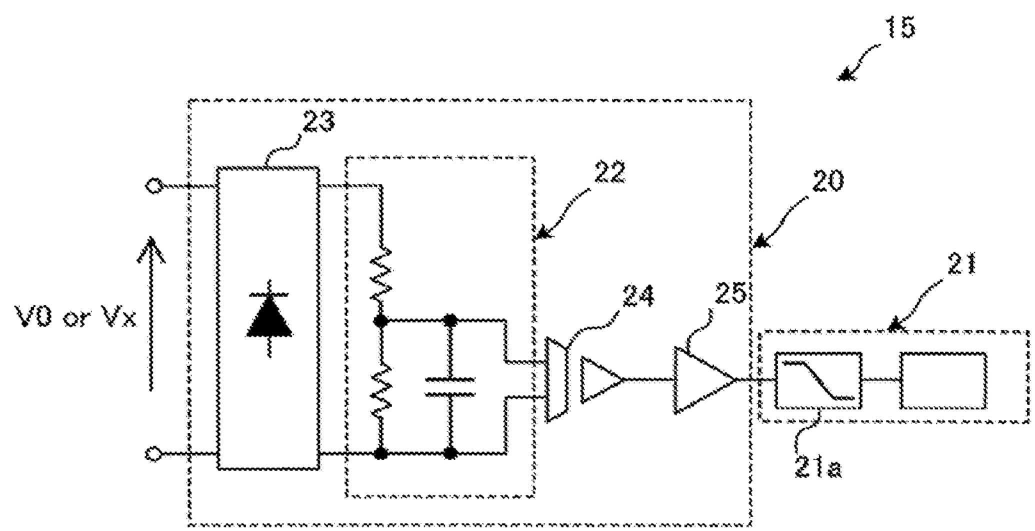
FIG. 4 is a diagram illustrating a configuration example of a detecting circuit in Embodiment 2 of the present invention.

Next, a little more specific description is given on the detecting circuit. The voltage detecting unit 21 is intended to receive a high-frequency AC voltage waveform as an input and detect an amplitude thereof. For example, an example of a configuration of the voltage detecting unit 21 is illustrated in FIG. 4. An AC signal input from the left of FIG. 4 is first allowed to pass through a detection-side rectifier circuit 23 to be converted to a one-polarity signal, that is, a signal that does not vary to the positive or negative and has only positive or negative polarity. This voltage is transformed to a low voltage suited for an IC and other elements by the voltage dividing circuit 22. The voltage transformed by the voltage dividing circuit 22 is input to the insulation amplifier 24. The insulation amplifier 24 is provided on the assumption that a potential of a detecting circuit 20 is different from a potential of a control system of the apparatus, but is not required when the potential of the detecting circuit 20 is the same as the potential of the control system of the apparatus. An output from the insulation amplifier 24 is then amplified by an amplifier 25 as required, and is input to the voltage detecting unit 21 of the control system through a low-pass filter 21*a*. The low-pass filter 21*a* is configured to remove a high frequency caused by inverter switching, but since a phenomenon to be observed is primarily a concentration of the refrigerant in the oil, a time constant of a change in the phenomenon is considered to be sufficiently long. Therefore, in order to increase detection accuracy, it is desired that averaging processing be performed by allowing the frequency of a filter to be sufficiently low, i.e. several Hz, for example, and by allowing the detection time to set sufficiently long, i.e. one second, for example.

In FIG. 4, the voltage dividing circuit 22 is provided next to the detection-side rectifier circuit 23, but a voltage of the same level as the bus voltage of the inverter 36 is applied as a detected voltage to the inverter power lines, for example, and hence a voltage of 100 V or more is generally applied. Therefore, in the configuration of FIG. 4, a corresponding withstanding pressure is required of the detection-side rectifier circuit 23. For example, when half-wave rectification or full-wave rectification of the diode is used, it is relatively easy for the detection-side rectifier circuit 23 to have a high withstanding pressure. Meanwhile, when analog signal processing by an operational amplifier or other device, or digital signal processing is used in the detection-side rectifier circuit 23, it is difficult to perform signal processing with a high voltage, and hence it is desired to provide the detection-side rectifier circuit 23 after the voltage dividing circuit 22.

Input impedance of the detecting circuit 20 is mainly determined by the voltage dividing circuit 22. It is required for the input impedance of the detecting circuit 20 to be sufficiently higher than impedance of the detection target, that is, a capacitor formed of the electrode F and the electrode G or the measuring capacitor 3. Although depending on a configuration method of the electrodes, when the electrodes F and G are included in the compressor 50, and a gap (for example, 1 mm or more) that is enough to allow the oil to flow therethrough is provided therein to form the capacitor, an electrostatic capacitance of the capacitor is at most 10 to several tens of pF. A PWM frequency of the inverter is often several kHz, and hence the impedance of the capacitor formed of the electrode F and the electrode G is 10 to several tens of MΩ. Therefore, it is required for the impedance of the voltage dividing circuit 22 to be a value that is at least equal to or larger than the impedance of the capacitor, for example, equal to or larger than 100 MΩ.

In Embodiment 1, it has been described that the PWM-controlled inverter is suitable for the present invention, and this is because the switching frequency (carrier frequency) of the inverter 36 is fairly high in the case of the PWM control. The present invention is applicable also to an inverter that is not PWM-controlled, but in that case, based on the discussion given above, with the impedance of the capacitor formed of the electrode F and the electrode G is increased when the switching frequency of the inverter is low, it is required for a detection system to have sufficiently high impedance.

As described above, in Embodiment 2, the electrostatic capacitance detection device 1 includes the electrode pair 2, which is formed of a pair of electrodes included in the liquid container (for example, shell housing 51 of the compressor 50), and the measuring capacitor 3 connected in series to the electrode pair 2. The electrostatic capacitance detection device 1 further includes the inverter 36, the liquid (for example, refrigerating machine oil 56), which is stored in the liquid container and is used in the device driven by the inverter 36, and the voltage detecting unit 21. The inverter 36 has the power line for driving the device (for example, compressor 50) or the bus connected to the one end of the electrode pair 2 and the measuring capacitor 3 connected in series (measurement target portion 8). Then, the voltage detecting unit 21 measures the voltage between the electrodes of the electrode pair 2.

As a result, as in Embodiment 1, the electrostatic capacitance detection device 1 can detect the electrostatic capacitance formed between the electrode pair 2 by applying the AC voltage of the inverter power lines, with the measuring capacitor 3, to the electrode pair 2 in the compressor 50. For example, the state of the oil (whether the oil is present or not, or is diluted with a liquid solvent) between the electrode pair 2 is detected.

Embodiment 3

Figure 5:
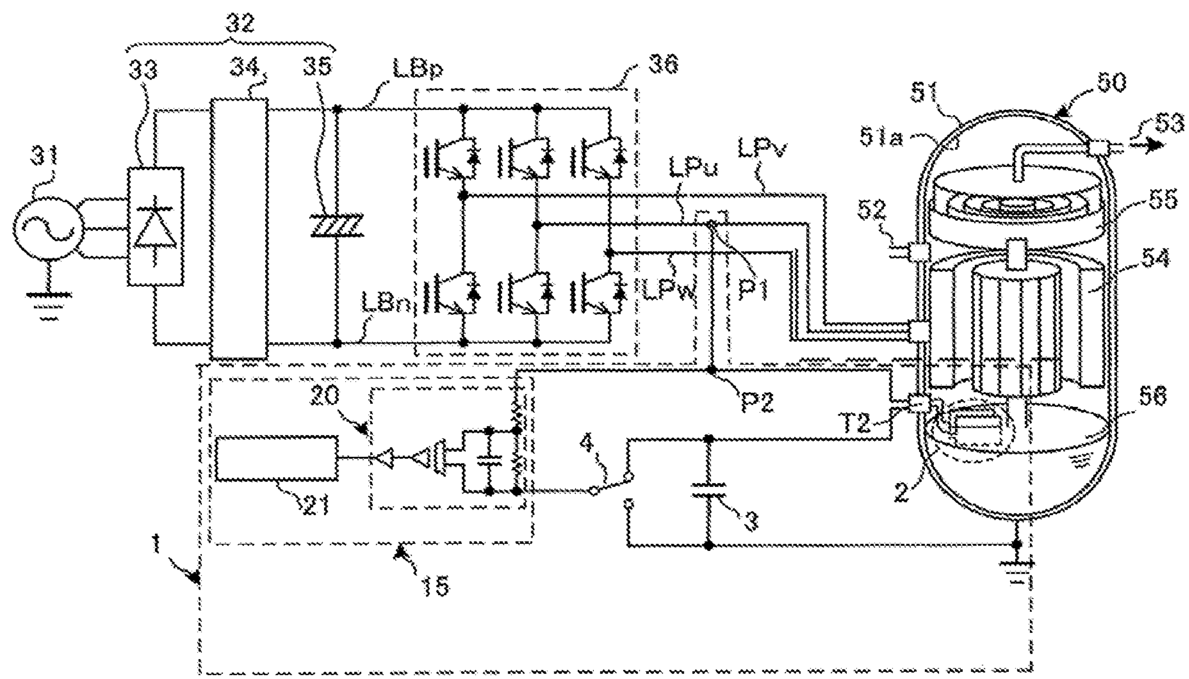
FIG. 5 is a diagram illustrating an installation configuration of an electrostatic capacitance detection device according to Embodiment 3 of the present invention.

FIG. 5 is a diagram illustrating an installation configuration of an electrostatic capacitance detection device according to Embodiment 3 of the present invention. A principle of this detection method is that electrodes as an electrostatic capacitance sensor and a capacitor having an explicit capacitance are connected in series to each other, and the AC voltage is applied to both ends of the series-connected electrode and capacitor to measure the electrostatic capacitance between the electrodes. In FIG. 1, the measuring capacitor 3 is connected to the power line LPu, and one end (electrode G) of the electrode pair 2 is connected to the ground, but as in FIG. 5, similar detection can be achieved also when the measuring capacitor 3 is connected to the ground, and the electrode pair 2 is connected to the power line LPu side, for example.

As described above, in Embodiment 3, the electrostatic capacitance detection device 1 includes the electrode pair 2, which is formed of a pair of electrodes included in the liquid container (for example, shell housing 51 of the compressor 50), and the measuring capacitor 3 connected in series to the electrode pair 2. The electrostatic capacitance detection device 1 further includes the inverter 36, the liquid (for example, refrigerating machine oil 56), which is stored in the liquid container and is used in the device driven by the inverter 36, and the voltage detecting unit 21. The inverter 36 has the power line for driving the device (for example, compressor 50) connected to the one end of the measurement target portion 8, which is the electrode pair 2 and the measuring capacitor 3 connected in series. Then, the voltage detecting unit 21 measures the voltage between the electrodes of the electrode pair 2.

As a result, as in Embodiment 1, the electrostatic capacitance detection device 1 detects the electrostatic capacitance formed between the electrode pair 2 by applying the AC voltage of the inverter power lines with the measuring capacitor 3 to the electrode pair 2 in the compressor 50. For example, the state of the oil (whether the oil is present or not, or is diluted with a liquid solvent) between the electrode pair 2 is detected.

Embodiment 4

Figure 6:
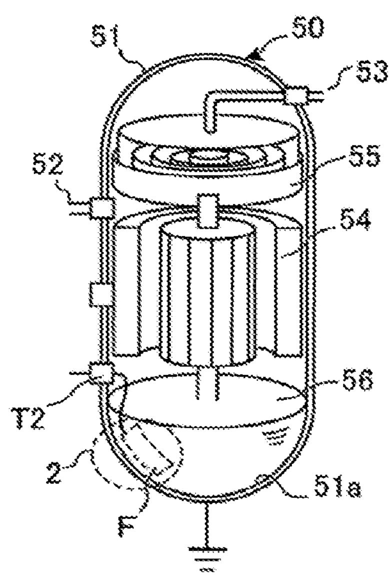
FIG. 6 is an illustration of a partial configuration of an electrostatic capacitance detection device according to Embodiment 4 of the present invention.

FIG. 6 is an illustration of a partial configuration of an electrostatic capacitance detection device according to Embodiment 4 of the present invention. In a circuit connection like that of FIG. 1, that is, in a case where the electrode G is connected to the shell housing 51 to have the ground potential, one of the electrodes has the same potential as the shell, and hence the shell housing 51 itself can be used as the electrode G. In other words, as in FIG. 6, only the electrode F is included in the compressor 50, and the electrode F may face a shell inner wall 51*a* with a small gap being present therebetween to form a capacitor between the electrode F and the shell inner wall 51*a*, for example. In this case, not only the number of extracted electrodes may be reduced to one, but also the configuration of the electrodes is significantly simplified such that an electrode having a large area can be included in a small space inside the compressor 50. The area of the electrode is proportional to a capacitance of the capacitor formed of the electrode F and the electrode G, and as the area becomes larger, the detection accuracy can be made higher.

As described above, in Embodiment 4, one (electrode G) of the electrodes of the electrode pair 2 is formed of the liquid container (for example, shell housing 51). Hence, one of the electrodes is the housing itself, and as a result, the structure of the electrodes is simplified, and it becomes easier to increase the electrode area.

Embodiment 5

Figure 7:
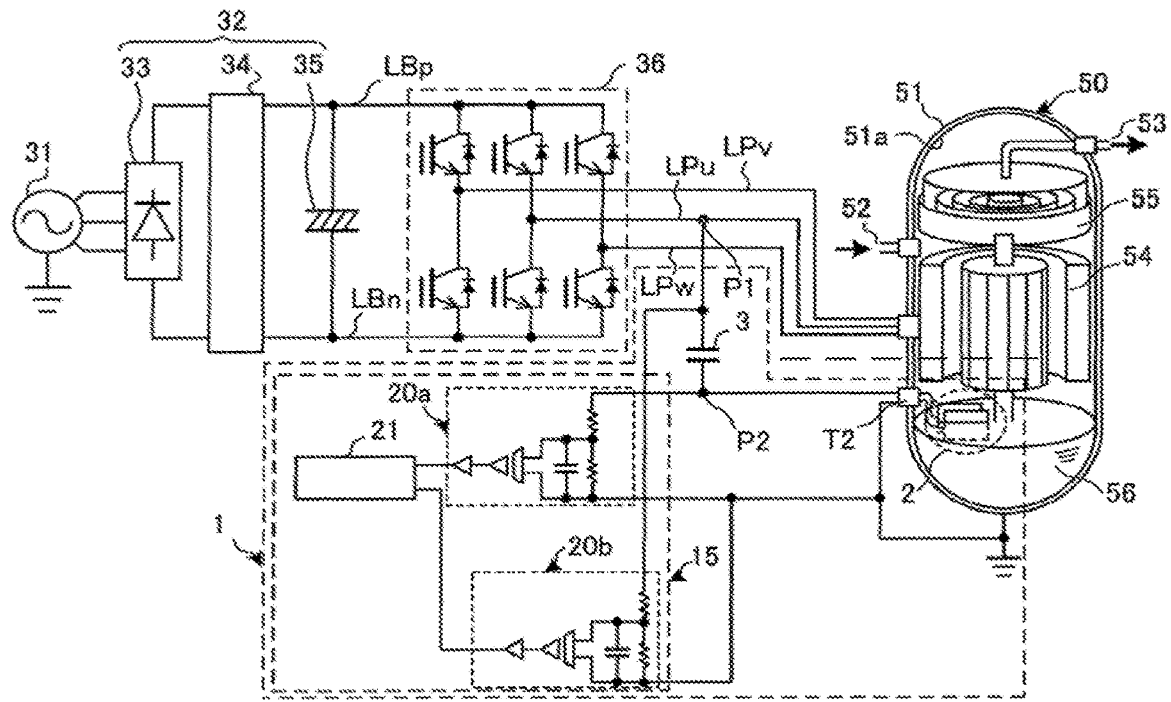
FIG. 7 is a diagram illustrating an installation configuration of an electrostatic capacitance detection device according to Embodiment 5 of the present invention.

FIG. 7 is a diagram illustrating an installation configuration of an electrostatic capacitance detection device according to Embodiment 5 of the present invention. In the present invention, the value of the electrostatic capacitance Cx is determined using the expression (1), and hence it is required to detect values of amplitudes of the voltage V0 and the voltage Vx. In FIG. 1, in order to detect the voltage Vx and the voltage V0, the relay 4 switches the detection target for one detecting circuit 20. This configuration has an advantage that only one detecting circuit 20 is required, but a large change in value of the voltage V0 may occur before and after the switching, or when the voltage V0 contains a long-term fluctuation, accurate measurement may not be performed. In order to solve such problems, a method is known in which a potential difference between the electrodes of the electrode pair 2 and a potential difference between both ends of the measurement target portion 8 are separately input to a plurality of detecting circuits 20*a* and 20*b* as in FIG. 7 to detect the voltages by the voltage detecting unit 21, for example. In such a voltage measurement device 15, two detecting circuits 20*a* and 20*b* are required. However, the relay 4 becomes unnecessary, and stable and highly accurate detection can be performed for the fluctuation of the voltage V0.

As described above, in Embodiment 5, the electrostatic capacitance detection device 1 further includes a first detecting circuit (detecting circuit 20*a*), to which the potential difference Vx between the electrodes of the electrode pair 2 is input, and a second detecting circuit (detecting circuit 20*b*), to which the potential difference V0 between both ends of the series-connected electrode pair 2 and measuring capacitor 3 is input. Then, the voltage detecting unit 21 detects the potential difference Vx between the electrodes of the electrode pair 2, which is input to the first detecting circuit, and the potential difference V0 between both ends of the measurement target portion 8, which is input to the second detecting circuit. As a result, the potential of the electrode F and the potential of the power line are required for the measurement of the electrostatic capacitance, but by providing different detectors to each of the detecting circuits, stable measurement can be performed without being affected by the long-term fluctuation in potential.

Embodiment 6

Figure 8:
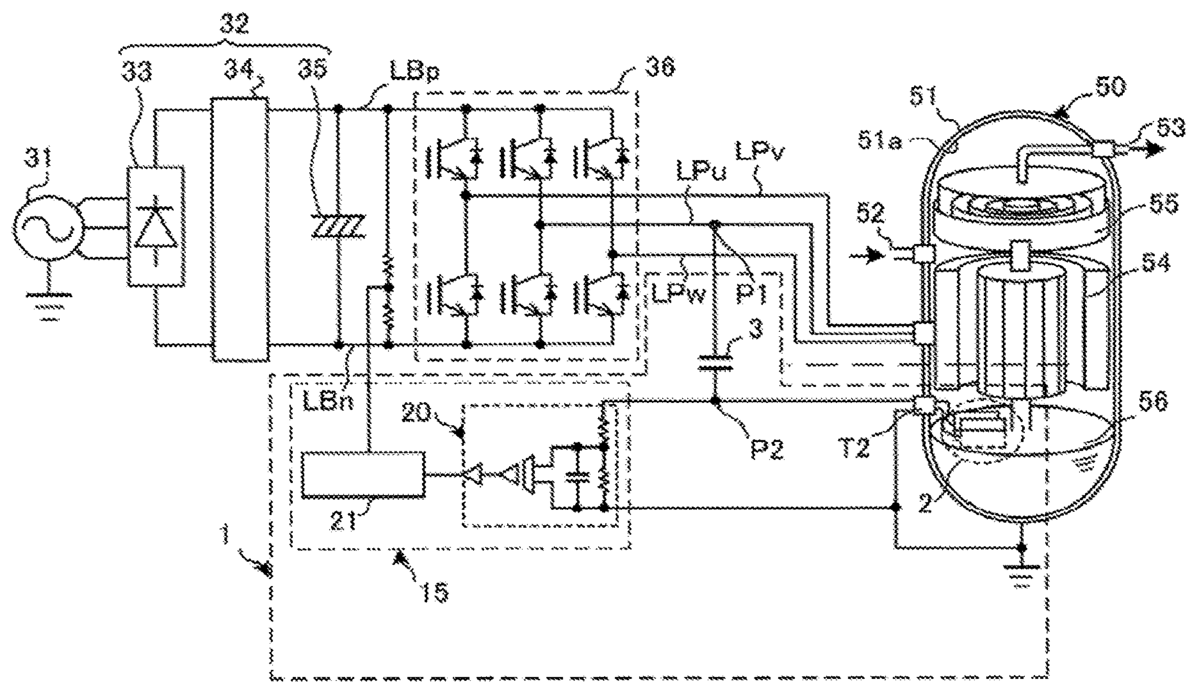
FIG. 8 is a diagram illustrating an installation configuration of an electrostatic capacitance detection device according to Embodiment 6 of the present invention.

FIG. 8 is a diagram illustrating an installation configuration of an electrostatic capacitance detection device according to Embodiment 6 of the present invention. A method as in FIG. 8 is also conceivable. This method involves detecting a value of the bus voltage of the inverter 36 instead of detecting the voltage V0. As shown in FIG. 2, the amplitude of the voltage output to the inverter power lines is basically an inverter bus voltage. Therefore, as long as the bus voltage of the inverter 36 is measured, the voltage V0 can be estimated based on the value of the bus voltage. The bus voltage of the inverter 36 is important in controlling the inverter 36, and hence is often detected for use in controlling the inverter 36 and the detected bus voltage is recognized by a control circuit.

As described above, in Embodiment 6, the electrostatic capacitance detection device 1 includes the voltage detecting unit 21 configured to detect a potential of a bus of the inverter 36, and is configured to detect the electrostatic capacitance of the electrode pair 2 based on the voltage between the electrodes of the electrode pair 2 and the potential of the bus of the inverter 36. As a result, both of the potential of the electrode F and a potential of a power line are required for measuring the electrostatic capacitance, but with a fluctuation range of the power line corresponding to the bus voltage of the inverter 36, when the inverter bus voltage is detected by another method, the bus voltage can also be used by the electrostatic capacitance detection device 1.

Embodiment 7

Figure 9:
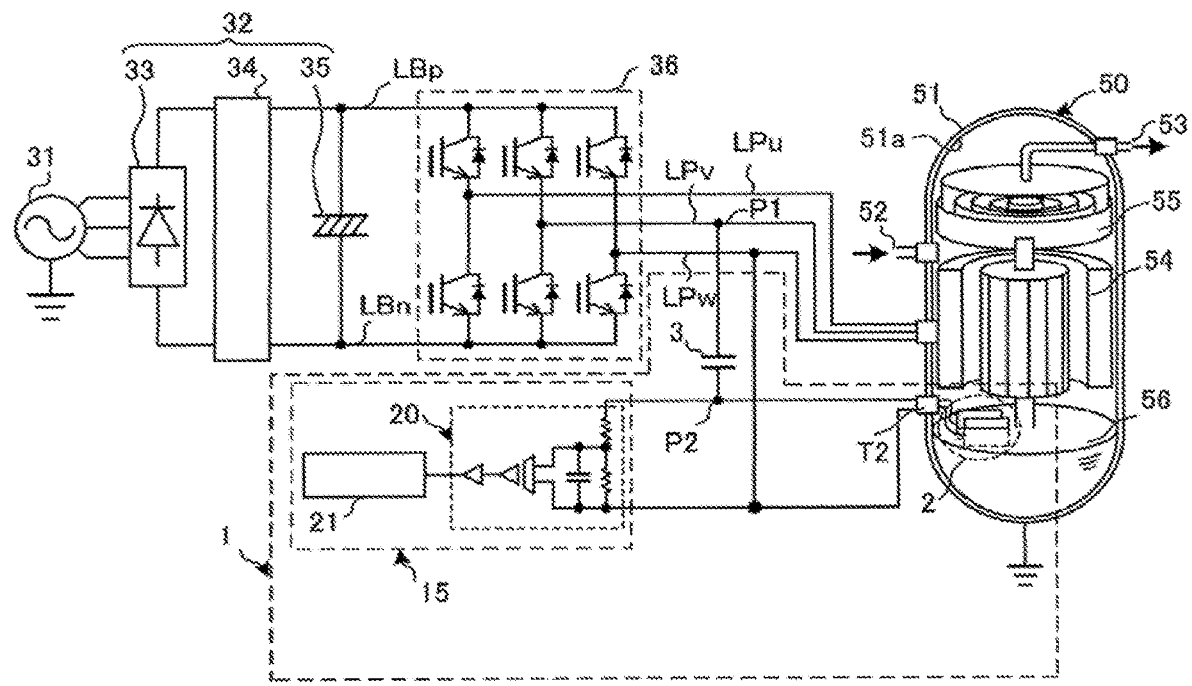
FIG. 9 is a diagram illustrating an installation configuration of an electrostatic capacitance detection device according to Embodiment 7 of the present invention.

FIG. 9 is a diagram illustrating an installation configuration of an electrostatic capacitance detection device according to Embodiment 7 of the present invention. As described in Embodiment 5, there are several methods of acquiring the voltage V0, such as measuring the voltage V0 after switching with the relay 4, separately measuring the voltage V0, and estimating the voltage V0 based on the bus voltage. Therefore, for the sake of simplicity, in the following examples, it is assumed that the voltage V0 is measured by the method as in FIG. 8, for example, and a description is given focusing only on a method of measuring the voltage Vx.

FIG. 9 is an example of a circuit configuration that is different from that of FIG. 1. In FIG. 1, of the electrode F and the electrode G, the electrode G is connected to the shell housing 51, that is, the ground potential. In FIG. 9, the electrode G is connected to the other one of the inverter power lines. In other words, the electrode F is connected to the measuring capacitor 3, the other end of the measuring capacitor 3 is connected to, for example, a V phase LPv of the inverter power lines, and the electrode G is connected to, for example, a W phase LPw other than the V phase LPv of the inverter power lines. In this case, the AC power source on the left side of the equivalent circuit of FIG. 3 corresponds to a line voltage between the V phase LPv and the W phase LPw of the power lines of the inverter 36. A line voltage of the inverter power lines is a voltage like the inverter output of FIG. 2, and contains the high-frequency component of the PWM. Therefore, the frequency component is voltage-divided by the capacitor in accordance with the circuit of FIG. 3 to determine the electrostatic capacitance Cx.

In the configuration of FIG. 1, the voltage between the inverter power line and the ground potential is used. In this case, a fluctuation component of a central potential of the inverter 36 is superimposed on the output voltage of the inverter 36. The "central potential of the inverter" as used herein is fluctuation of a potential between the N-bus LBn or the P-bus LBp of the inverter and the ground, and generally fluctuates at the frequency of the AC power source. Therefore, in the case of FIG. 1, the potential of the power line is a sum obtained by adding, to the fluctuation caused by the switching of the inverter 36, the fluctuation component of the central potential at the frequency of the AC power source, and the fluctuation may affect the measurement.

In contrast, when the line potential of the inverter power lines is used for the measurement as in FIG. 9, stable and highly accurate measurement can be performed without being affected by the fluctuation of the central potential of the inverter.

As described above, in Embodiment 7, the inverter 36 includes the power lines of a plurality of phases, and the electrode pair 2 and the measuring capacitor 3 connected in series has one end connected to a first phase (for example, V phase) of the plurality of phases, and the other end connected to a second phase (for example, W phase) of the plurality of phases. As a result, with both ends of the measurement target portion 8 being connected to different phases of the power lines, respectively, the line voltage of the power lines is applied to the measuring capacitor 3 and the electrode pair 2, and hence, an electrostatic capacitance detection device 1 can detect the electrostatic capacitance between the electrodes. In this case, there is obtained an effect of not being susceptible to the fluctuation in potential with respect to the ground of the inverter 36.

Embodiment 8

Figure 10:
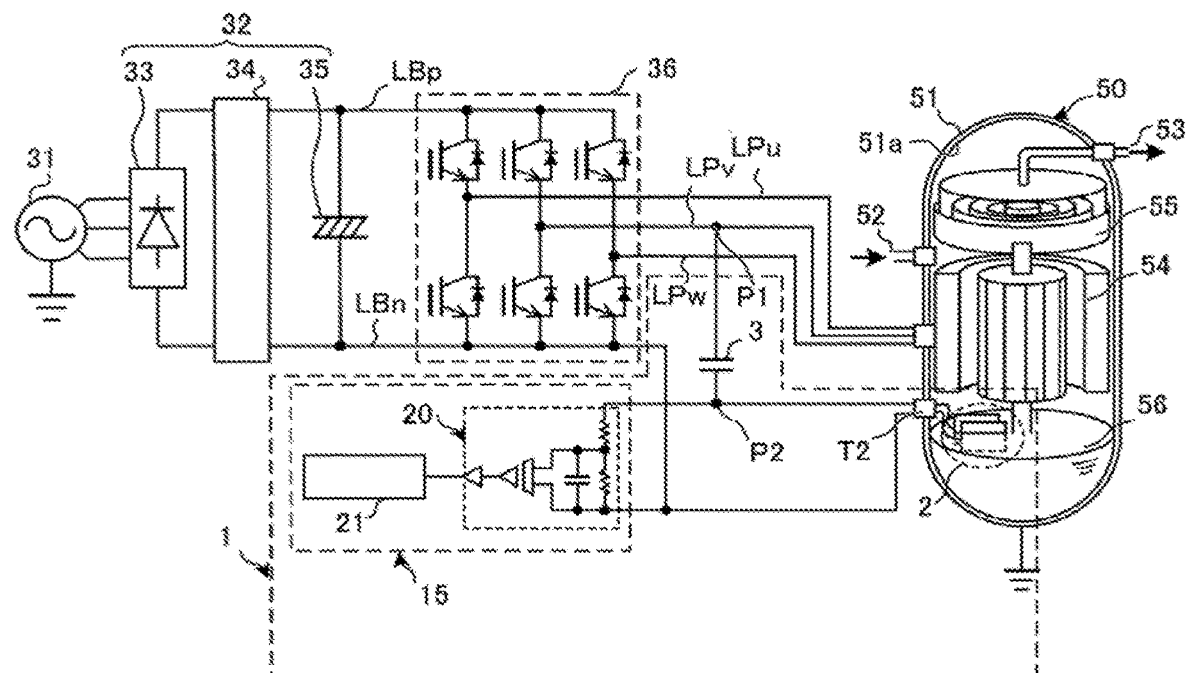
FIG. 10 is a diagram illustrating an installation configuration of an electrostatic capacitance detection device according to Embodiment 8 of the present invention.

Another method of the circuit connection is described. FIG. 10 is a diagram illustrating installation configuration of an electrostatic capacitance detection device according to Embodiment 8 of the present invention. FIG. 10 illustrates an example in which, similarly, the electrode G is connected to the N-bus LBn of the inverter. In this case, the AC power source of FIG. 3 corresponds to a potential of an inverter power line (for example, V phase) with respect to the N-bus LBn, and more specifically, a voltage (collector-emitter voltage) between both ends of an element on the N side of the V phase of the three-phase inverter as in FIG. 10. This voltage is also not affected by the fluctuation of the central potential of the inverter, and hence stable and highly accurate detection can be performed as in FIG. 9. Moreover, in the case of the configuration illustrated in FIG. 10, an N-bus potential is often taken as a control potential of the inverter, and hence the circuit configuration may be more simplified with the detecting circuit requiring no insulation amplifier or insulation power supply, for example.

As described above, in Embodiment 8, the series-connected electrode pair 2 and measuring capacitor 3 (measurement target portion 8) has one end connected to a power line of the inverter 36, and the other end connected to a bus (for example, N-bus LBn) of the inverter 36. As a result, the AC voltage generated by the switching of the inverter 36 is applied to the electrode pair 2, and the electrostatic capacitance between the electrodes can be detected based on the AC voltage. In this case, an effect of not being susceptible to the fluctuation in potential with respect to the ground of the inverter 36 is obtained. Another effect is also obtained that the potential of the detecting circuit becomes the N-bus potential.

Embodiment 9

Figure 11:
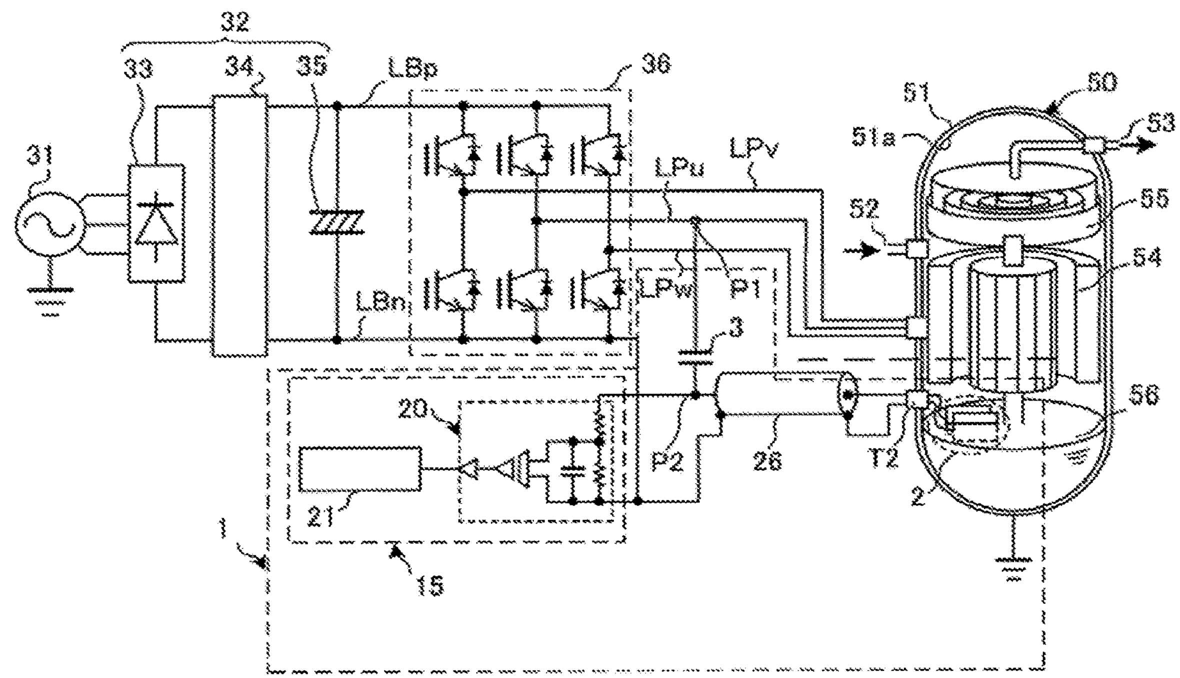
FIG. 11 is a diagram illustrating an example of an installation configuration of an electrostatic capacitance detection device according to Embodiment 9 of the present invention.
Figure 12:
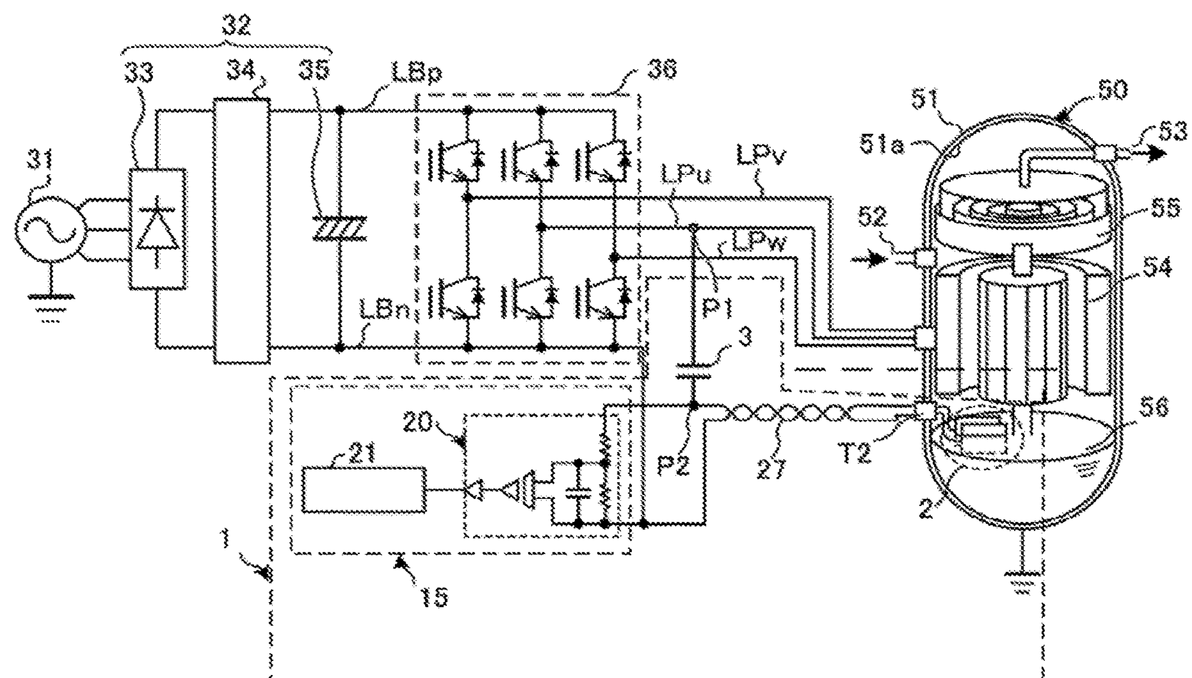
FIG. 12 is a diagram illustrating another example of the installation configuration of the electrostatic capacitance detection device according to Embodiment 9 of the present invention.

FIG. 11 is a diagram illustrating an example of an installation configuration of an electrostatic capacitance detection device according to Embodiment 9 of the present invention. FIG. 12 is a diagram illustrating another example of the installation configuration of the electrostatic capacitance detection device according to Embodiment 9 of the present invention. FIG. 11 and FIG. 12 illustrate, taking the configuration of FIG. 10 (method in which the electrode G is taken at the N-bus potential) as an example, a method in which a detection line from the compressor 50 and the detecting circuit 20 are connected to each other. In this example, the configuration of FIG. 10 is taken as an example, but similar effects can be obtained also for the configuration of FIG. 9 and the configuration of FIG. 1.

In FIG. 11, lines from the electrode F and the electrode G are connected to a coaxial cable 26 and brought to the detecting circuit 20. When the detecting circuit 20 is arranged also near the compressor 50, wiring of a detection signal does not pose significant problem, but when the detecting circuit 20 is provided near the inverter 36, for example, cables for a certain length are required. However, when an electrostatic capacitance between the cables fluctuates due to routing of the cables, structural problem, and other causes, the electrostatic capacitance becomes the floating capacitance that exists in parallel to the electrostatic capacitance Cx in the equivalent circuit of FIG. 3 to affect the detection accuracy. Therefore, it is required to reduce such fluctuation of the capacitance component caused by the cables, in particular, as much as possible. With the use of the coaxial cable 26 for the cables as in FIG. 11, the capacitance component that floats in parallel between the electrodes does not fluctuate even when the coaxial cable 26 is moved, and hence stable detection can be performed.

However, although the coaxial cable 26 minimizes a floating capacitance component with the shell housing 51 or a structure, the floating capacitance component between the two cables of the electrode F and the electrode G is relatively large. The floating capacitance component between the two cables reduces detection accuracy of the electrostatic capacitance Cx. Therefore, for example, in FIG. 12, the two cables is formed of a twisted pair cable 27. A floating capacitance between two lines is sufficiently small also for the coaxial cable, and sufficient stability can be achieved for routing of the cables.

As described above, in Embodiment 9, the electrode pair 2 and the voltage detecting unit 21 are connected to each other through the coaxial cable 26 or the twisted pair cable 27. As a result, with the use of the coaxial cable 26 or other cable for the connection of the electrode pair 2 and the voltage detecting unit 21, the floating electrostatic capacitance component caused by the cables is fixed, and hence highly accurate detection can be performed in the electrostatic capacitance detection device 1.

Embodiment 10

In Embodiment 10, a power conversion apparatus 100 and an electrostatic capacitance detection device 1 have configurations similar to those of FIG. 1. For example, in an outdoor unit of an air-conditioning apparatus, when the compressor is stopped under a low-temperature state, a phenomenon called "refrigerant stagnation phenomenon" occurs, in which the refrigerant is collected in the compressor 50 to increase a refrigerant concentration inside the refrigerating machine oil 56. The refrigerant stagnation phenomenon is a typical case in which an abnormality in refrigerant concentration adversely affects the operation of the compressor, and it is another object of the present invention to detect this state. However, in the present invention, the detection is performed with the equivalent circuit of FIG. 3, but a power supply of the equivalent circuit is an AC power source generated by the switching of the inverter 36. Therefore, in order to perform the detection, it is required for the inverter 36 to be in operation. In other words, with the method of the present invention, the detection cannot be performed when the inverter is stopped.

At such startup and other occasions, when the detection in the present invention is to be performed under the state in which the compressor 50 is not in operation, it is conceivable to use locked energization. The "locked energization" is a method of energizing a winding of a compressor motor 54 at the halt under such a condition that the compressor 50 cannot be operated, and the compressor 50 can be preliminary heated through the locked energization. For example, Patent Literature 2 (WO 2014/188566 A1) discloses a technology in which a carrier frequency of an inverter is set to a frequency that is higher than a normal frequency to allow only a high-frequency current to flow without rotating a motor of a compressor. With the compressor of Patent Literature 2, a winding of the motor is heated to heat the oil in which the refrigerant stagnates, to thereby evaporate the refrigerant and bring the state of the oil closer to a normal state. When the inverter performs high-frequency switching, the detection in the present invention can be performed. Therefore, when it is required to perform the detection under the state in which the rotation of the motor 54 is stopped, the locked energization may be performed.

Taking as an example the control at startup of the compressor 50 and the use of the locked energization, an example of control using the detection method of the present invention is described. When the compressor is started in the related-art technology, the locked energization for a certain time at the startup and other control have been performed in consideration of a risk that a large amount of refrigerant is dissolved (stagnates) in the oil. However, with such control, the locked energization for the certain time is performed even when the stagnation does not occur, and hence the startup has taken time.

In contrast, when the present invention is applied, the concentration of the refrigerant in the oil can be detected, and hence the following control can be performed. Specifically, first, when the air-conditioning apparatus is started, the locked energization is performed in consideration of the risk of stagnation before the compressor 50 is operated. The concentration of the refrigerant is detected in accordance with the present invention while the locked energization is performed. When the concentration of the refrigerant reaches a normal value, the locked energization is stopped and the compressor 50 is operated. Through such control, the time for the locked energization at the startup is minimized, and a startup period is significantly reduced.

As described above, in Embodiment 10, in the electrostatic capacitance detection device 1, under the state in which the compressor 50 stops the compression operation, the voltage having the frequency that is higher than a PWM control frequency during the compression operation is applied to the compressor 50 from the inverter 36, and the voltage between the electrodes is detected. As a result, through the application of such high frequency that the compressor 50 cannot be rotated, the power conversion apparatus 100 can detect the state during a period in which the compressor is stopped.

Embodiment 11

Figure 13:
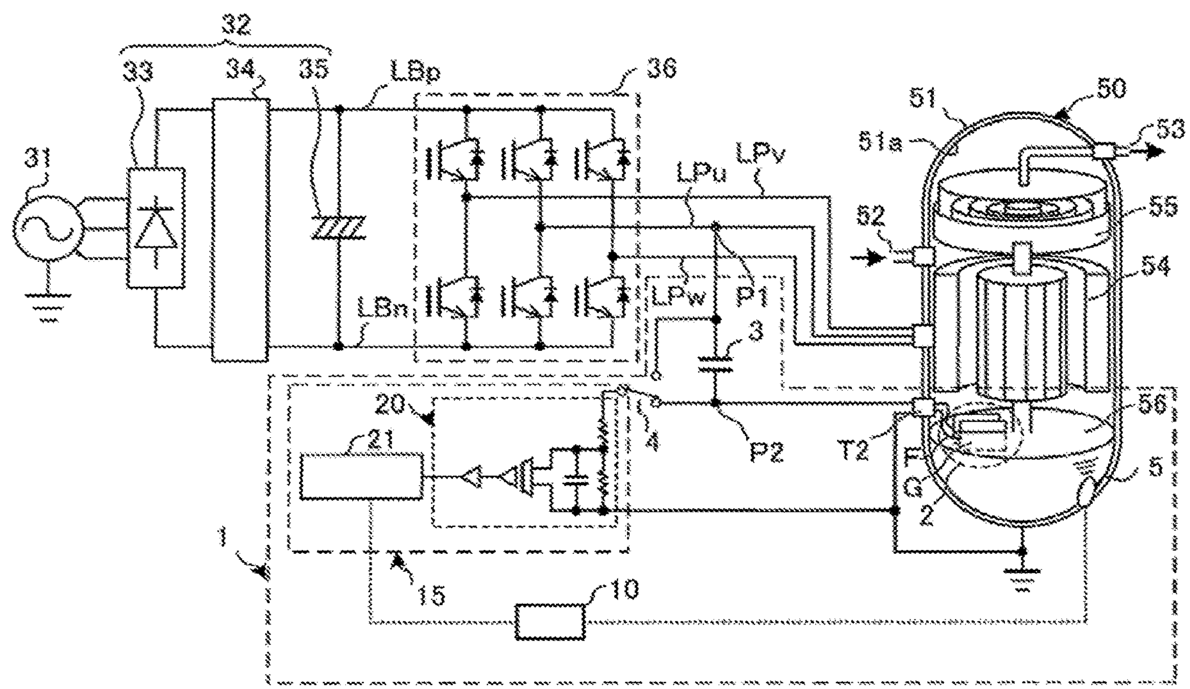
FIG. 13 is a diagram illustrating an installation configuration of an electrostatic capacitance detection device according to Embodiment 11 of the present invention.

FIG. 13 is a diagram illustrating an installation configuration of an electrostatic capacitance detection device according to Embodiment 11 of the present invention. In Embodiment 11, the electrostatic capacitance detection device 1 further includes a temperature sensor 5 and a control unit 10, and is configured to be able to detect a concentration. Parts having the same configurations as those in Embodiment 1 are denoted by the same reference symbols, and a description thereof is omitted.

Figure 14:
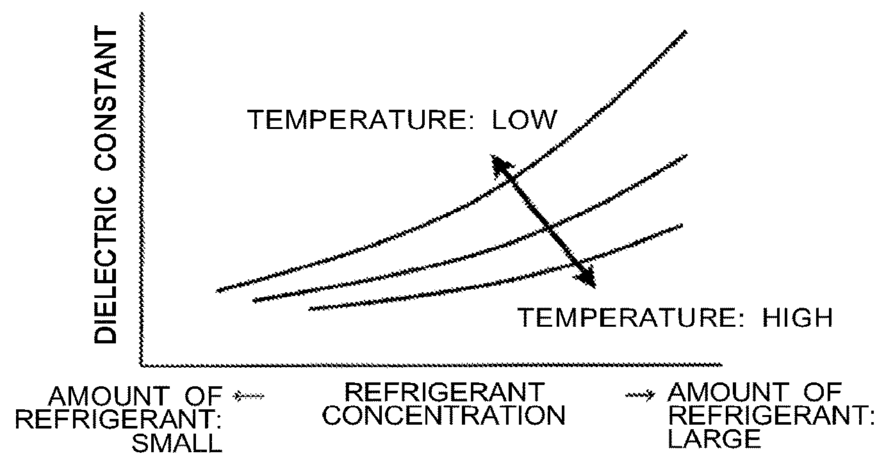
FIG. 14 is a graph showing temperature dependence of an oil relative dielectric constant-refrigerant concentration relationship, which is stored in a control unit in Embodiment 11 of the present invention.

FIG. 14 is a graph showing temperature dependence of an oil relative dielectric constant-refrigerant concentration relationship, which is stored in the control unit in Embodiment 11 of the present invention. FIG. 14 shows a change in dielectric constant in a case where the refrigerant is dissolved in the refrigerating machine oil 56. The dependence is changed depending on the type of the oil or the refrigerant, and hence FIG. 14 is merely an example. As in this example, the dependence of the dielectric constant on the refrigerant concentration may have strong dependence on the temperature in some cases. In such case, in order to measure the refrigerant concentration, not only the dielectric constant but also information on the temperature is required. In this case, it is preferred that data as in FIG. 14 be first stored in a form of a table or an approximation in the control unit 10. Then, a method can be taken in which, in combination with a result of measuring a relative dielectric constant with the electrostatic capacitance obtained by the measurement in the present invention, the temperature of the oil is measured with a thermocouple or a thermistor, for example, or the temperature of the oil is estimated by another method to estimate the concentration of the refrigerant.

As described above, in Embodiment 11, the compressor 50 stores a blend of the oil and the refrigerant in which the refrigerant is dissolved in the oil (for example, refrigerating machine oil 56), and includes the temperature sensor 5 configured to measure the temperature of the refrigerant in which the oil is dissolved, and the control unit 10 in which the temperature dependence of the dielectric constant of the oil and the dielectric constant of the refrigerant is stored. The control unit 10 is configured to detect the concentration of the refrigerant or the concentration of the oil based on the temperature of the oil in which the refrigerant is dissolved, which is measured by the temperature sensor 5, the voltage measured by the voltage detecting unit 21, and the temperature dependence. As a result, with the relative dielectric constant of the refrigerant being dependent on the temperature, the electrostatic capacitance detection device 1 can increase the detection accuracy by correcting the refrigerant concentration with the temperature when detecting the refrigerant concentration.

Embodiment 12

The present invention is aimed at detecting the state of the refrigerating machine oil 56 in the compressor 50. The detection of the state is performed in order to, for example, detect whether the oil is present or not (oil depletion sensing), detect the height of a liquid level of the oil (oil level sensing), or detect how much refrigerant is dissolved in the oil (refrigerant concentration detection). It is important to determine a position at which the electrostatic capacitance sensor is arranged, that is, the electrode pair 2 in the compressor 50 depending on the purpose. For example, when the oil depletion is to be sensed, the height of the oil level should be located at a height that is the same as, or a little higher than that of the intake port of the oil. When the oil level sensing is to be performed, it is conceivable to arrange a sensor that is long in the height direction, or that is divided into several parts in the height direction.

Meanwhile, when the refrigerant concentration is to be detected, it is desired to arrange a sensor near the bottom of the compressor 50. For example, when the sensor is arranged near the oil intake port, it becomes difficult to distinguish a change in electrostatic capacitance from a change in oil level and a change in electrostatic capacitance with a change in refrigerant concentration. When the sensor is arranged near the bottom of the compressor 50, it can be considered that the oil level is always located at a position that is higher than the sensor, and that the electrode pair 2 as the sensor is completely immersed in the oil, and as a result, only the change in refrigerant concentration can be measured without being affected by the change in oil level.

Moreover, the above discussion is made relating to the case in which the compressor 50 is placed vertically and the oil is stored below the motor as in FIG. 1, and needless to say, when the compressor is placed horizontally, sensor position is required to be contrived depending on the horizontal position.

As described above, in Embodiment 12, the liquid container is a housing of the compressor 50, and the liquid is any one of the following liquid: the refrigerant, the oil, or the oil in which the refrigerant is dissolved. Embodiment 12 is intended to detect the state of the oil in the compressor 50. The compressor 50 driven by the motor includes an electric mechanism, the oil, and the refrigerant, and hence includes elements required to detect the liquid state by the electrostatic capacitance detection device 1.

Embodiment 13

Figure 15:
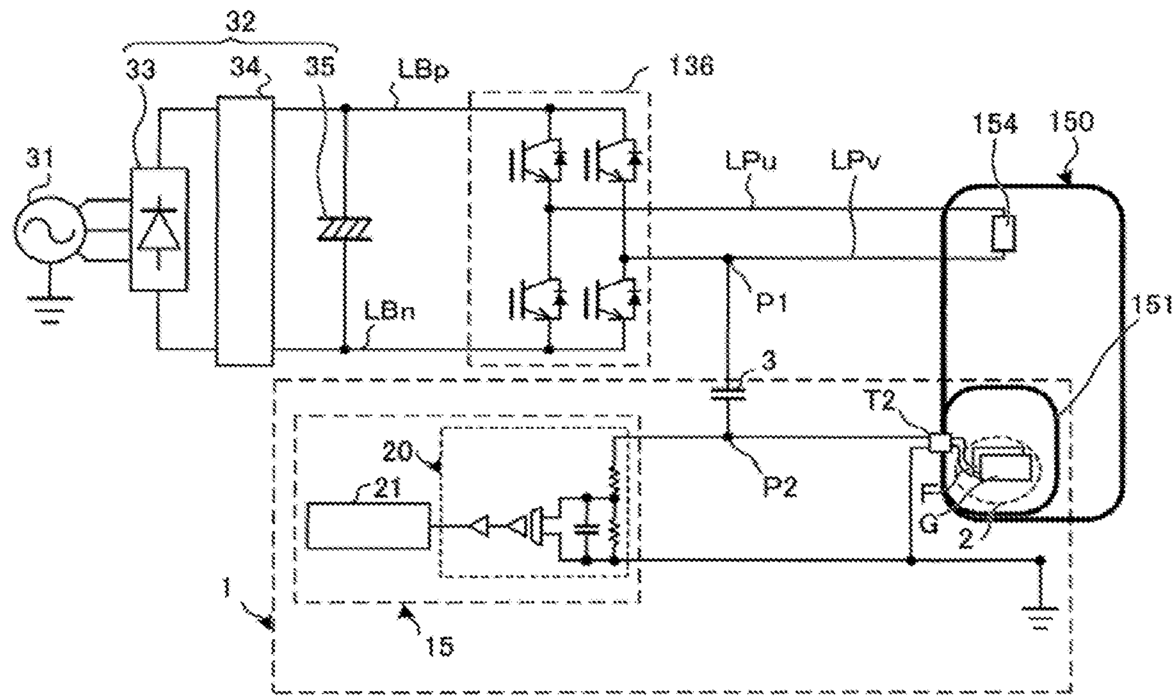
FIG. 15 is a diagram illustrating an installation configuration of an electrostatic capacitance detection device according to Embodiment 13 of the present invention.

FIG. 15 is a diagram illustrating an installation configuration of an electrostatic capacitance detection device according to Embodiment 13 of the present invention. In the embodiments described above, there has been described the case in which the motor is driven with the use of the inverter having the three-phase power lines as in FIG. 1, for example. The present invention is applicable not only to the inverter having the three-phase power lines, but also to a single-phase inverter, a full-bridge inverter, a half-bridge inverter, or an inverter of the other form. One example of the inverter of the other form is illustrated in FIG. 15.

A circuit configuration between the three-phase AC power source 31 and the inverter 136, and a configuration of the electrostatic capacitance detection device 1 are similar to the configurations in the embodiments described above, and a description thereof is omitted to avoid duplication. Embodiment 13 is different from the embodiments described above in the configuration of the inverter and a load device to be driven.

In FIG. 15, a single-phase full-bridge inverter drives a load 154. In the case of the three-phase inverter, there are three power lines: a U phase, the V phase, the W phase, but a single-phase inverter 136 in Embodiment 13 has two power lines LPu and LPv of the U phase and the V phase, respectively. Here, a load device 150 is not the motor or other device, which is generally driven in three phases, but an AC load, for example, an induction heater or an ozonizer.

Moreover, in a case where the load device 150 is driven by the single-phase inverter 136, a full-bridge inverter, or other inverter, when an AC voltage is generated for stepping up or down in a power conversion circuit, the electrostatic capacitance detection device may use the generated AC voltage. Separately from the load 154, an electrostatic capacitance detection device 1 configured to detect a state of liquid used in the load device 150 is provided inside a liquid container 151 in the load device 150. In FIG. 15, a configuration in which the liquid container 151 is provided inside the load device 150 is adopted, but a configuration in which the liquid container 151 is provided outside the load device 150 may be adopted. In FIG. 15, one electrode of the electrode pair 2 of the electrostatic capacitance detection device 1 is connected to the ground potential, and the other electrode is connected to LPv, which is one of the two power lines, via the measuring capacitor 3.

In FIG. 15, the electrostatic capacitance detection device 1 of FIG. 8 is applied to a power line of a single-phase inverter. Similarly to FIG. 8, the voltage between the power line and the ground is divided by the measuring capacitor 3 and the electrode pair 2 of the electrostatic capacitance detection device 1 such that the value of the electrostatic capacitance can be obtained. Moreover, a similar configuration is applicable to a case in which the potential between the two power lines is used as illustrated in FIG. 9, or the case in which the potential between the power line and the N-bus is used as illustrated in FIG. 10.

As described above, in Embodiment 13, the electrostatic capacitance detection device 1 includes the electrode pair 2 including a pair of electrodes, which are included in the liquid container 151, and the measuring capacitor 3, which is connected in series to the electrode pair 2. The electrostatic capacitance detection device 1 further includes the inverter 136, the liquid stored in the liquid container 151 for use in the apparatus driven by the inverter 136, and the voltage detecting unit 21. The inverter 136 has the power line or the bus for driving a device (for example, load device 150) connected to the one end of the series-connected electrode pair 2 and measuring capacitor 3 (measurement target portion 8), and the voltage detecting unit 21 measures the voltage between the electrodes of the electrode pair 2.

From the above description, the electrostatic capacitance detection device 1 can be applied to not only the compressor but also various devices to be driven by the inverter. As in Embodiment 1, the electrostatic capacitance detection device 1 uses the AC voltage of the inverter power lines, and applies, with the measuring capacitor 3, the AC voltage to the electrode pair 2, to thereby detect the electrostatic capacitance formed between the electrodes of the electrode pair 2. Therefore, the electrostatic capacitance detection device 1 can also be used for liquid level detection in the liquid container, or for detection of a concentration of the liquid mixture.

Embodiment 14

Figure 16:
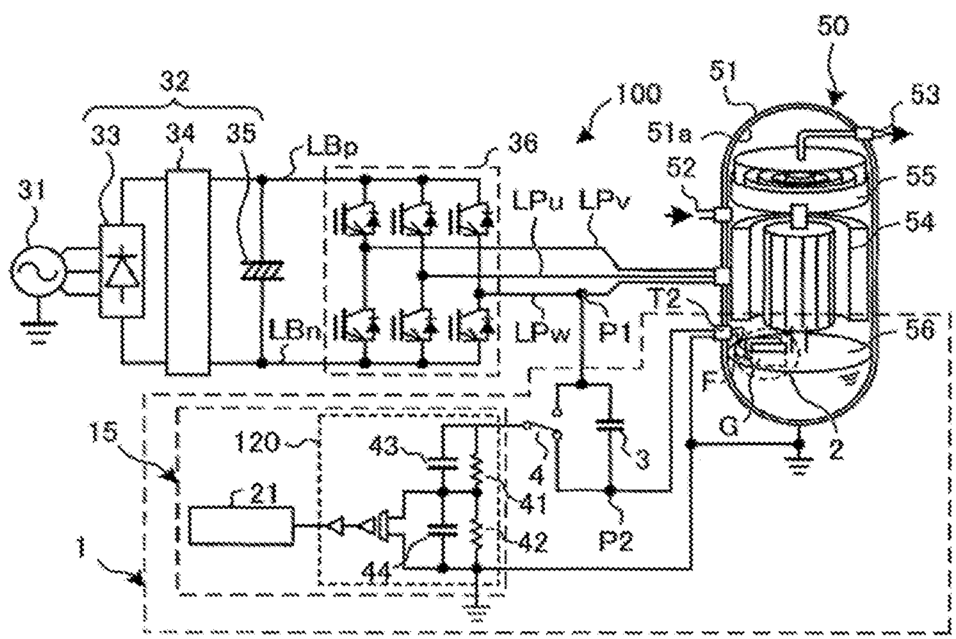
FIG. 16 is a diagram illustrating an installation configuration of an electrostatic capacitance detection device and a power conversion apparatus according to Embodiment 14 of the present invention.
Figure 17:
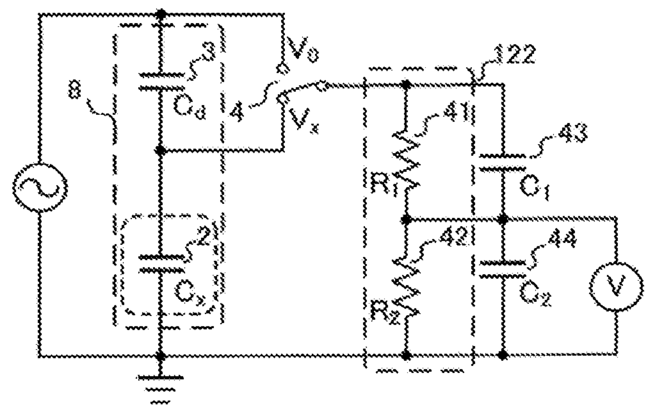
FIG. 17 is a diagram illustrating an equivalent circuit as a detection principle in Embodiment 14 of the present invention.

FIG. 16 is a diagram illustrating an installation configuration of an electrostatic capacitance detection device and a power conversion apparatus according to Embodiment 14 of the present invention. FIG. 17 is a diagram illustrating an equivalent circuit as a detection principle in Embodiment 14 of the present invention. In Embodiment 14, an AC voltage between one (for example, power line LPw) of the plurality of power lines LPu, LPv, and LPw, which connect the inverter 36 and the compressor 50 to each other, and the ground is divided by the electrostatic capacitances of the measuring capacitor 3 and the electrode pair 2 to measure the electrostatic capacitance of the electrode pair 2. In the following description, parts having the same configurations as those in Embodiment 1 are denoted by the same reference symbols, and a description thereof is omitted.

Incidentally, in an actual air-conditioning apparatus, various kinds of noise are superimposed on the voltage waveform of the power lines, and the switching of the inverter 36 is substantially close to a rectangular wave. Therefore, a pulse-like rush current flows through the measuring capacitor 3 and the electrode pair 2 by a sharp rise of voltage.

In the detecting circuit 20 illustrated in FIG. 1, the voltage of the measurement target is divided by resistors and input to the voltage detecting unit 21. When a voltage having a waveform with a sharp rise is applied to such a voltage divider resistor circuit, the voltage dividing by the resistors may not work satisfactorily because of a minute floating capacitance of the detecting circuit 20.

Therefore, in Embodiment 14, as illustrated in FIG. 16 and FIG. 17, a detecting circuit 120 includes a plurality of resistors for dividing the voltage, and a plurality of capacitors for dividing the voltage. Specifically, a first resistor 41 and a second resistor 42 are connected in series to each other to form a voltage dividing circuit 122, to thereby divide the detected voltage. Moreover, a first capacitor 43 and a second capacitor 44 are connected in parallel to the first resistor 41 and the second resistor 42, respectively. Hereinafter, a resistance of the first resistor 41 is represented by R1, a resistance of the second resistor 42 is represented by R2, a capacitance of the first capacitor 43 is represented by C1, and a capacitance of the second capacitor 44 is represented by C2. A voltage dividing ratio k of the circuit is defined by the following expression (2).

$$k = \frac{R1}{R1 + R2} \tag{2}$$

The first capacitor 43 has a function of reducing the effect of the floating capacitance of the circuit. The second capacitor 44 has a function of reducing fluctuation of the detected voltage caused by the floating capacitance and the capacitance C1 in the sharp rising portion of the voltage. When attention is focused on the capacitance C1 and the capacitance C2, the voltage of the measurement target is divided by the first capacitor 43 and the second capacitor 44, and hence a condition in which a voltage dividing ratio of the capacitor unit becomes equal to the voltage dividing ratio k of the above-mentioned resistances is expressed by the following expression (3).

$$k = \frac{R1}{R1 + R2} = \frac{C1}{C1 + C2} \tag{3}$$

$$R1 \times C1 = R2 \times C2 \tag{4}$$

When the capacitance C1 and the capacitance C2 satisfy the condition, the voltage is theoretically divided by the voltage dividing ratio k in all frequency range, and hence a waveform similar to a waveform input to the detecting circuit 120 is detected. As a value of the capacitance C1, it is required to select a value larger than the floating capacitance that is parallel to the first capacitor 43 in terms of reducing the effect of the floating capacitance that exists in parallel to the first capacitor 43. It should be noted, however, that a series capacitance of the first capacitor 43 and the second capacitor 44 is parallel to the electrostatic capacitance Cx of the electrode pair 2 as the measurement target, and hence when the value of the capacitance C1 is too large, the detected value is affected. As the value of the capacitance C1, a value that is larger than the floating capacitance and is smaller than Cx, specifically, 1 pF to several tens of pF is suitable.

When the capacitance C1 is determined, the capacitance C2 is determined based on the relational expression (3) or expression (4) above. However, when the floating capacitance that is parallel to the first capacitor 43 is taken into consideration, the value of the capacitance C2 under the condition in which the voltage dividing ratio of the voltage-dividing capacitors is equal to the above-mentioned voltage dividing ratio k is larger than the value of the capacitance C2 calculated by the expression (4) to be exact. Therefore, it is desired that the value of the capacitance C2 of the second capacitor 44 be set to a value larger than C2 given by the expression (4).

Moreover, when the input switching waveform has a sharp rise, and the voltage dividing circuit 122 voltage-divides the input waveform extremely accurately, a detected voltage waveform after the voltage division also has a sharp rise. In this case, it is required that the detecting circuit on the voltage detecting unit 21 side of the voltage dividing circuit 122 be formed of circuit elements having good high-frequency characteristics. In that case, the value of the capacitance C2 that is set in consideration of the floating capacitance may be set even larger to delay the rise of the waveform after the voltage division, and expensive broad-band circuit elements become unnecessary.

As described above, the electrostatic capacitance detection device 1 according to Embodiment 14 includes the voltage dividing circuit 122, which includes the first resistor 41 and the second resistor 42 connected in series to each other, is connected in parallel to the electrode pair 2 as the measurement target, and is configured to voltage-divide the electrode pair 2. The electrostatic capacitance detection device 1 also includes the first capacitor 43 connected in parallel to the first resistor 41, and the second capacitor 44 connected in parallel to the second resistor 42.

Moreover, the resistance R1 of the first resistor 41, the resistance R2 of the second resistor 42, the capacitance C1 of the first capacitor, and the capacitance C2 of the second capacitor satisfy the condition: R1×C1=R2×C2, and more preferably satisfy the condition: R1×C1<R2×C2.

Embodiment 15

As described above, with the switching close to the rectangular waveform of the inverter 36 and the sharp voltage rise of the noise component, pulse-like inrush current flows through the measuring capacitor 3 and the electrode pair 2. In order to remove such a high-frequency component, the low-pass filter 21*a* is provided in FIG. 4, but it is desired to remove such a high-frequency fluctuation component in a stage prior to the detecting circuit 20.

Figure 18:
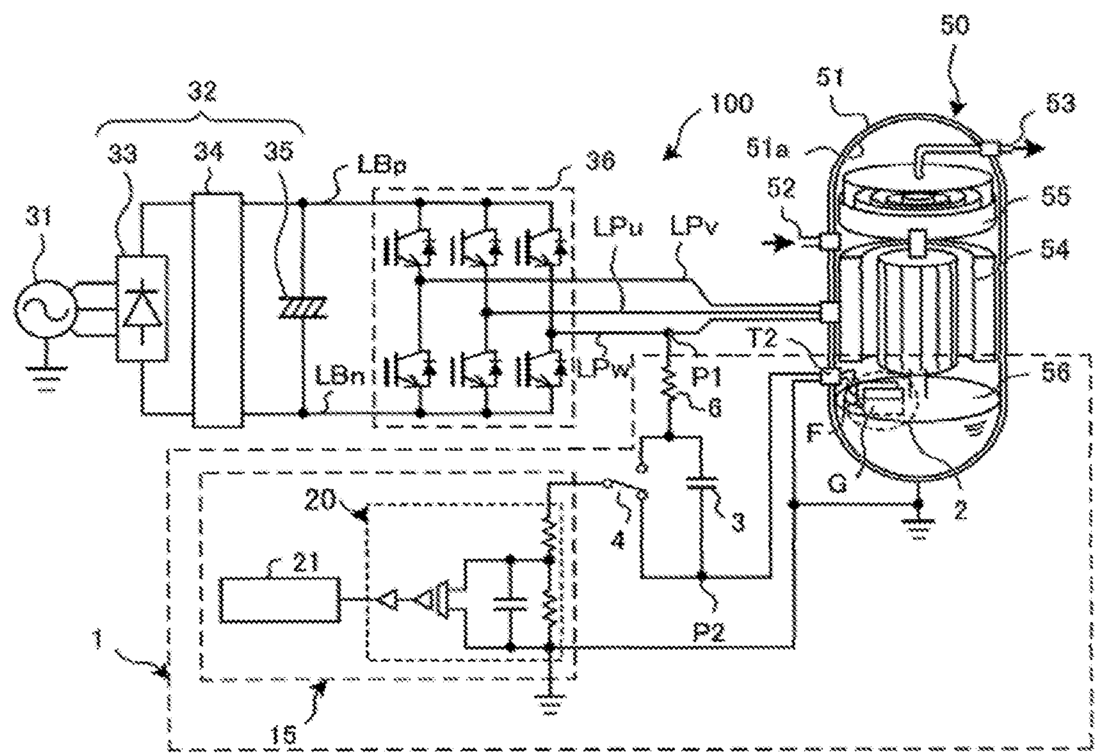
FIG. 18 is a diagram illustrating an installation configuration of an electrostatic capacitance detection device and a power conversion apparatus according to Embodiment 15 of the present invention.
Figure 19:
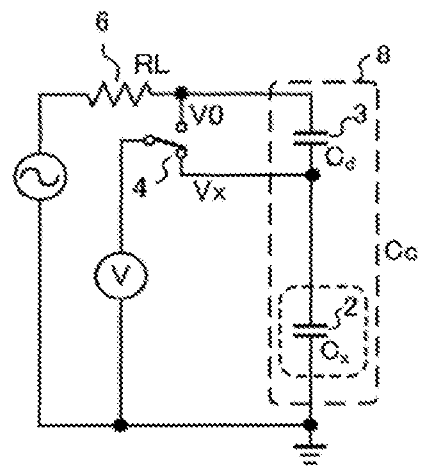
FIG. 19 is a diagram illustrating an equivalent circuit as a detection principle in Embodiment 15 of the present invention.

FIG. 18 is a diagram illustrating an installation configuration of an electrostatic capacitance detection device and a power conversion apparatus according to Embodiment 15 of the present invention. FIG. 19 is a diagram illustrating an equivalent circuit as a detection principle in Embodiment 15 of the present invention. In Embodiment 15, in order to remove the above-mentioned high-frequency fluctuation component, the electrostatic capacitance detection device 1 includes a filtering resistor 6. In the following, parts having the same configurations as those in Embodiment 1 are denoted by the same reference symbols, and a description thereof is omitted.

As illustrated in FIG. 18 and FIG. 19, the one end of the measurement target portion 8 is connected to the power line LPw, and the filtering resistor 6 is provided between the power line LPw and the measuring capacitor 3 of the measurement target portion 8. As a result, a resistance of the filtering resistor 6 and the electrostatic capacitances of the measuring capacitor 3 and the electrode pair 2 form a kind of low-pass filter. Therefore, a voltage waveform from which a sharp high-frequency component is removed is input to the one end of the measurement target portion 8, and hence the effect of such a high-frequency component can be reduced in the voltage measurement device 15. There has been described the case in which the measuring capacitor 3 is connected to the power line LPw of the W phase via the filtering resistor 6, but instead of being connected to the power line LPw of the W phase, the measuring capacitor 3 may be connected to the power line LPv of the V phase or the power line LPu of the U phase.

A combined electrostatic capacitance Cc of the measuring capacitor 3 and the electrode pair 2 is expressed by the following expression (5) using the electrostatic capacitance Cx of the electrode pair 2 and the electrostatic capacitance Cd of the measuring capacitor 3.

$$Cc = \frac{Cd \times Cx}{Cd + Cx} \tag{5}$$

As described in Embodiment 2, when the combined electrostatic capacitance Cc is about 10 to about several tens of pF, impedance of the measurement target portion 8 is several MΩ to several hundreds of kΩ. When a resistance value RL of the filtering resistor 6 is sufficiently large with respect to the impedance of the measurement target portion 8, the voltage of the power line LPw is mostly applied to the filtering resistor 6, and the voltage between both ends of the measurement target portion 8, which is the voltage used for the detection, is reduced, which is not suitable for the detection. Meanwhile, when the resistance value RL of the filtering resistor 6 is sufficiently small with respect to the impedance of the measurement target portion 8, a sufficient effect as the low-pass filter cannot be obtained. In other words, as the resistance value of the filtering resistor 6, a value of the same level as the combined electrostatic capacitance Cc of the measuring capacitor 3 and the electrode pair 2 to a value that is about 1/100th of the combined electrostatic capacitance Cc, desirably a value that is about 1/10th of the combined electrostatic capacitance Cc is desired. When a PWM frequency of the inverter 36 is represented by f, such a range of the resistance value RL of the filtering resistor 6 is expressed using the combined electrostatic capacitance Cc as follows.

$$\frac{1}{2\pi fCc} > RL > 0.01 \times \frac{1}{2\pi fCc} \tag{6}$$

As described above, in the electrostatic capacitance detection device 1 according to Embodiment 15, the filtering resistor 6 is installed at at least one of the following positions: between the electrode pair 2 and the measuring capacitor 3, at the one end of the measurement target portion 8, and at the other end of the measurement target portion 8. Specifically, the filtering resistor 6 may be provided at the position between the electrode pair 2 and the measuring capacitor 3, or the position between the one end of the measurement target portion 8 and a first power line (for example, power line LPw). Alternatively, the filtering resistor 6 may be provided at a position between the other end of the measurement target portion 8 and a ground potential point, between the other end of the measurement target portion 8 and a bus of the inverter, or between the other end of the measurement target portion 8 and a second power line (power line LPu, LPv).

As a result, the electrostatic capacitance detection device 1 can remove the high-frequency fluctuation component caused by the switching of the inverter 36 by the filtering resistor 6 in the stage prior to the detecting circuit 20, and reduce the effect on the detection.

Embodiment 16

Figure 20:
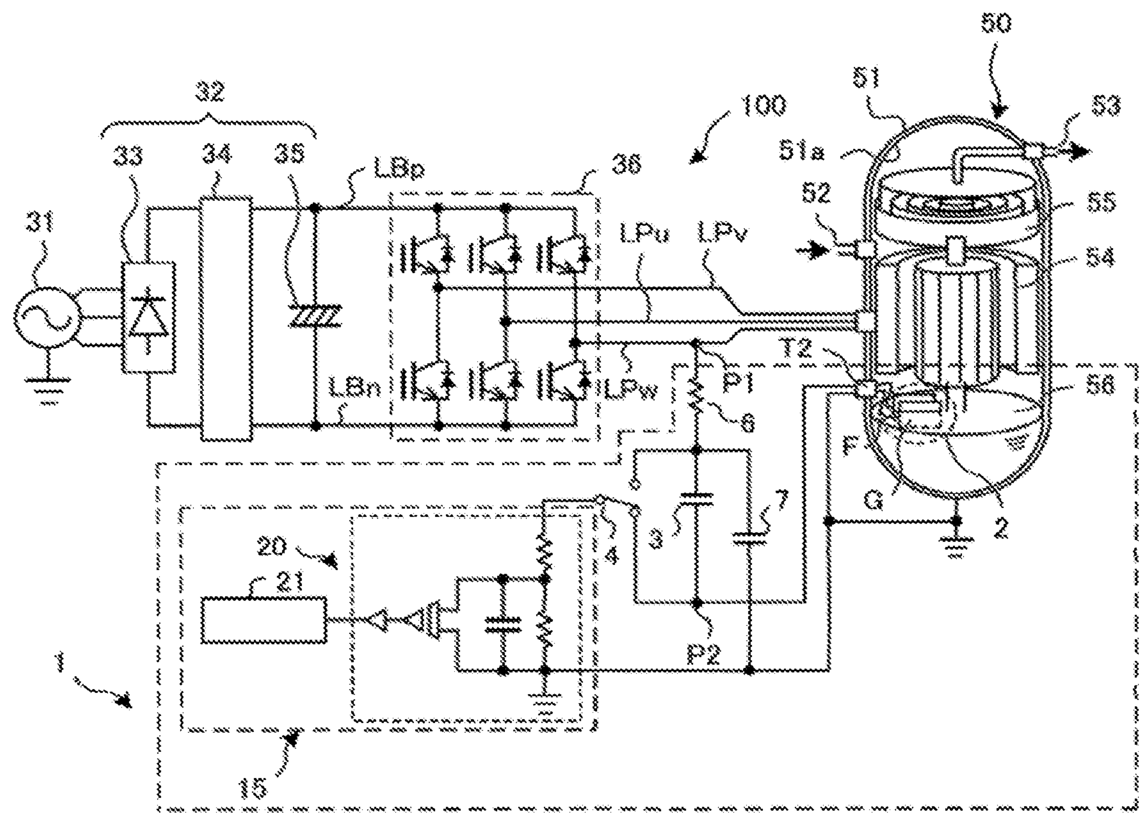
FIG. 20 is a diagram illustrating an installation configuration of an electrostatic capacitance detection device and a power conversion apparatus according to Embodiment 16 of the present invention.
Figure 21:
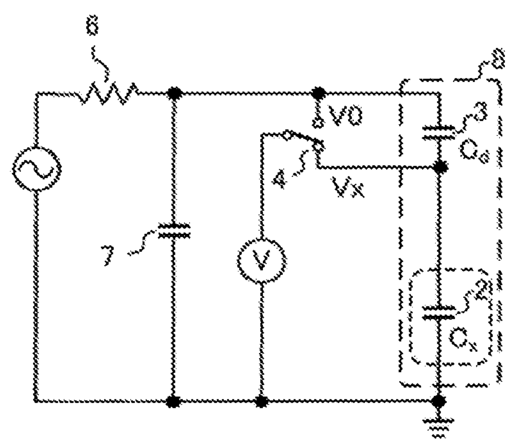
FIG. 21 is a diagram illustrating an equivalent circuit as a detection principle in Embodiment 16 of the present invention.

FIG. 20 is a diagram illustrating an installation configuration of an electrostatic capacitance detection device and a power conversion apparatus according to Embodiment 16 of the present invention. FIG. 21 is a diagram illustrating an equivalent circuit as a detection principle in Embodiment 16 of the present invention. In Embodiment 16, the electrostatic capacitance detection device 1 further includes an auxiliary capacitor 7. In the following, parts having the same configurations as those in Embodiment 1 are denoted by the same reference symbols, and a description thereof is omitted.

In Embodiment 15, the filtering resistor 6 having the resistance value RL that is the same level as the impedance of the combined electrostatic capacitance Cc of the measuring capacitor 3 and the electrode pair 2 or smaller than the combined electrostatic capacitance Cc is selected. However, the electrostatic capacitance of the measurement target portion 8 has impedance as high as several MΩ, and the entire electrostatic capacitance is further increased by adding the filtering resistor 6 in series thereto. As a result, when the filtering resistor 6 is installed, the electric current that flows through the electrode pair 2 serving as the sensor may be reduced, and the detection may become difficult.

To address the above-mentioned problem, in Embodiment 16, as illustrated in FIG. 20, the auxiliary capacitor 7 is provided in parallel to the measurement target portion 8, which is formed of the measuring capacitor 3 and the electrode pair 2. When the auxiliary capacitor 7 is added as described above, the electrostatic capacitance detection device 1 can increase a combined capacitance of the parallel connection of the measurement target portion 8 and the auxiliary capacitor 7, and reduce the resistance value RL of the filtering resistor 6. As a result, the electrostatic capacitance detection device 1 can improve S/N (signal-to-noise ratio) of the detection as compared to the case of Embodiment 15.

Embodiment 17

In Embodiment 1, the measuring capacitor 3 and the electrode pair 2 are directly connected to each other, and the series-connected measuring capacitor 3 and electrode pair 2 (measurement target portion 8) is connected to the power line. In Embodiment 17, there is described a case in which the measuring capacitor 3 and the electrode pair 2 form a series circuit together with other two capacitors. In the following, parts having the same configurations as those in Embodiment 1 are denoted by the same reference symbols, and a description thereof is omitted.

Figure 22:
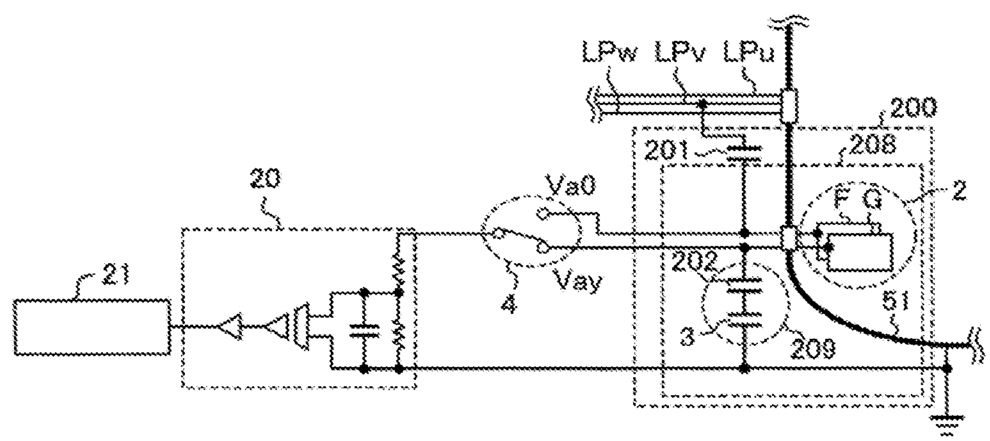
FIG. 22 is a diagram illustrating a connection state of an electrostatic capacitance detection device to a power line in Embodiment 17 of the present invention.

FIG. 22 is a diagram illustrating a connection state of an electrostatic capacitance detection device according to Embodiment 17 of the present invention to a power line. The shell housing 51 of the compressor 50 is only partially illustrated. The power line LPu, the power line LPv, and the power line LPw are connected to the compressor 50. Although not shown, the power line LPu, the power line LPv, and the power line LPw are connected to the inverter 36 as in the case of FIG. 1. Moreover, the electrode pair 2 is arranged inside the shell housing 51.

As illustrated in FIG. 22, the electrode F forming the electrode pair 2 is connected to the power line LPv via a first relay capacitor 201. Meanwhile, the electrode G is connected to the measuring capacitor 3 with a second relay capacitor 202 being present therebetween. Moreover, the measuring capacitor 3 is connected to the ground potential point or the shell housing 51 having the ground potential. Here, the first relay capacitor 201, the electrode pair 2, the second relay capacitor 202, and the measuring capacitor 3 form a sequence of series circuit 200. A portion formed of the electrode pair 2, the second relay capacitor 202, and the measuring capacitor 3 is hereinafter referred to as a "measurement target portion 208" of the series circuit 200, and a portion formed of the second relay capacitor 202 and the measuring capacitor 3 is referred to as a "comparison target portion 209".

The sequence of series circuit 200 has one end connected to the power line LPv, and the other end connected to the ground potential point or the ground potential. In Embodiment 17, the other end of the series circuit 200 is connected to the ground potential point, but may be connected to a bus of the inverter 36, or the power line LPu or the power line LPw of a phase that is different from that of the power line LPv.

The voltage detecting unit 21 is connected to the relay 4 with the detecting circuit 20 being present therebetween. The relay 4 switches the detection target between a potential Va0 between both ends of the measurement target portion 208 and a potential Vay between both ends of the comparison target portion 209 of the series circuit 200. Here, a capacitor having a known capacitance is used as each of the measuring capacitor 3, the first relay capacitor 201, and the second relay capacitor 202. The first relay capacitor 201 and the second relay capacitor 202 may be a part of another circuit, or may be a sensor. The series circuit 200 may further include a resistor. The resistor is connected between the measurement target portion 208 and the ground potential point, for example.

Then, an electrostatic capacitance detection device 1 can calculate the electrostatic capacitance of the electrode pair 2 by detecting and comparing the potential difference between both ends of the measurement target portion 208 of the series circuit 200, and the potential difference between both ends of the comparison target portion 209, which is a portion obtained by excluding the electrode pair 2 from the measurement target portion 208. In Embodiment 17, in particular, the potential difference between both ends of the comparison target portion 209 is measured, and hence the electrostatic capacitance detection device 1 can calculate the potential difference Vx between both ends of the electrode pair 2, calculate a capacitance of the electrode pair 2, and further calculate the electrostatic capacitance of the electrode pair 2.

As described above, also in a case where the electrode pair 2 and the measuring capacitor 3 are not directly connected to each other, when the sequence of series circuit 200 is formed, the electrostatic capacitance detection device 1 can sense the electrostatic capacitance of the electrode pair 2 as in the case of Embodiment 1. It is only required that the measuring capacitor 3 and the electrode pair 2 form the series circuit 200, and that the series circuit 200 have one end connected to the power line LPv of the inverter 36, and the other end connected to the ground potential point, a power line of another phase (for example, power line LPu or power line LPw), or the bus. With such a configuration, the electrostatic capacitance detection device 1 measures the potential difference between both ends of the measurement target portion 208 including the electrode pair 2 and the comparison target portion 209, and measures the potential difference of the comparison target portion 209. Then, the electrostatic capacitance detection device 1 can calculate the electrostatic capacitance of the electrode pair 2 by subtracting the potential difference of the comparison target portion 209 from the potential difference of the measurement target portion 208, and comparing the potential difference of the measurement target portion 208 with the potential difference of the comparison target portion 209.

Here, the measurement target portion 208 may be the electrode pair 2, and the comparison target portion 209 may be one measuring capacitor 3. Moreover, when the series circuit 200 includes a resistor, the resistor may be connected between the series-connected second relay capacitor 202 and electrode pair 2 and the line LPv through a connection line including the resistor. Moreover, the resistor may be connected between the series-connected second relay capacitor 202 and electrode pair 2 and the power line LPw or the power line LPu, the ground potential point, or the bus of the inverter through a connection line including the resistor.

Moreover, the configuration can also be described as follows. One end of the series-connected electrode pair 2 and second relay capacitor 202 may not necessarily be connected to the power line LPv through a conductor. In other words, also in a case where the connection is established through a connection line including a capacitor (for example, first relay capacitor 201) therebetween, effects similar to those of Embodiment 1 can be obtained.

Moreover, the other end of the series-connected electrode pair 2 and second relay capacitor 202 may not necessarily be connected to the power line LPw or the power line LPu, the ground potential point, or the bus of the inverter through a conductor. In other words, even when the connection is established through a connection line including a capacitor (for example, measuring capacitor 3) therebetween, effects similar to those of Embodiment 1 can be obtained.

Moreover, even when a resistor or another capacitor is connected between the measuring capacitor 3 and the electrode pair 2, as long as the measuring capacitor 3 and the electrode pair 2 are connected in series to each other, effects similar to those in the case of Embodiment 1 can be obtained. Therefore, as long as one of the power lines of the inverter 36 and any one of a power line of another phase, the ground potential point, and the bus of the inverter are connected in series to each other with by the resistor, the capacitor, and the electrode pair 2 as the measurement target, the electrostatic capacitance can be detected through the above-mentioned measurement.

In this specification, the term "connection" means not only connection through a conductor, but also connection with a capacitor or a resistor being present therebetween. Here, the number of resistors and capacitors may be plural or single. Moreover, a capacitor or a resistor may be connected between the measuring capacitor 3 and the electrode pair 2 as the measurement target. Moreover, a capacitor or a resistor may be connected between the connection of the measuring capacitor 3 and the electrode pair 2 and the power line of the inverter 36, or between the connection of the measuring capacitor 3 and the electrode pair 2 and the ground potential point or the bus of the inverter.

REFERENCE SIGNS LIST

1 electrostatic capacitance detection device 2 electrode pair 3 measuring capacitor 4 relay 5 temperature sensor 6 filtering resistor 7 auxiliary capacitor 8 measurement target portion 10 control unit 15 voltage measurement device 20, 20*a*, 20*b* detecting circuit 21 voltage detecting unit

21*a* low-pass filter 22 voltage dividing circuit 23 detection-side rectifier circuit 24 insulation amplifier 25 amplifier 26 coaxial cable 27 twisted pair cable 31 three-phase AC power source 32 converter circuit 33 rectifier circuit 34 booster circuit 35 smoothing capacitor 36, 136 inverter 41 first resistor 42 second resistor 43 first capacitor 44 second capacitor 50 compressor 51 shell housing 51*a* shell inner wall 52 intake port 53 discharge port 54 motor 55 positive-displacement compressor 56 refrigerating machine oil 100 power conversion apparatus 150 load device

151 liquid container 154 load 200 series circuit 201 first relay capacitor 202 second relay capacitor 208 measurement target portion

209 comparison target portion Cx, Cd electrostatic capacitance Cs floating capacitance F, G electrode LBn N-bus LBp P-bus LPu, LPv, LPw power line (V phase, W phase, U phase) T2 glass terminal Vx, V0 voltage

The invention claimed is:

1. An electrostatic capacitance detection device, comprising:

an electrode pair including a pair of electrodes, the electrode pair being arranged inside a compressor configured to compress refrigerant;

a capacitor being connected in series to the electrode pair via a terminal disposed at a junction of an interior and exterior of the compressor;

an inverter having a first power line connected to one end of a measurement target portion, and being configured to drive the compressor, the first power line being one of power lines for driving the compressor, the measurement target portion being formed by a combination of the electrode pair and the capacitor connection in series to each other; and a voltage detecting unit configured to measure a voltage between the pair of electrodes of the electrode pair.

2. The electrostatic capacitance detection device of claim 1, further comprising a voltage detecting unit configured to detect a voltage between both ends of the measurement target portion, wherein the electrostatic capacitance detection device is configured to detect an electrostatic capacitance of the electrode pair based on the voltage between the pair of electrodes of the electrode pair and the voltage between both ends of the measurement target portion.

3. The electrostatic capacitance detection device of claim 1, wherein the measurement target portion has a second end being connected to any one of a ground potential point, a bus of the inverter, and a second power line of a phase that is different from a phase of the first power line.

4. The electrostatic capacitance detection device of claim 1, further comprising:

a voltage dividing circuit including a first resistor and a second resistor, and being connected in parallel to the electrode pair, the first resistor and the second resistor being connected in series to each other;

a first capacitor being connected in parallel to the first resistor; and a second capacitor being connected in parallel to the second resistor.

5. The electrostatic capacitance detection device of claim 4, wherein the following relationship is satisfied:

$$R1\times C1=R2\times C2 \text{ or } R1\times C1<R2\times C2,$$

where R1 is a resistance value of the first resistor, R2 is a resistance value of the second resistor, C1 is a capacitance of the first capacitor, and C2 is a capacitance of the second capacitor.

6. The electrostatic capacitance detection device of claim 1, further comprising a filtering resistor provided for at least one of the following positions: a position between the electrode pair and the capacitor; a position between the one end of the measurement target portion and the first power line; and a position between another end of the measurement target portion and a ground potential point, a bus of the inverter, or a second power line of a phase that is different from a phase of the first power line.

7. The electrostatic capacitance detection device of claim 6, further comprising an auxiliary capacitor connected in parallel to the measurement target portion.

8. The electrostatic capacitance detection device of claim 1, further comprising a switching mechanism configured to switch a detection target of the voltage detecting unit between the voltage between the pair of electrodes of the electrode pair and a voltage between both ends of the measurement target portion.

9. The electrostatic capacitance detection device of claim 1, further comprising a voltage detecting unit configured to detect a potential of a bus of the inverter, wherein the electrostatic capacitance detection device is configured to detect an electrostatic capacitance of the electrode pair based on the voltage between the pair of electrodes of the electrode pair and the potential of the bus of the inverter.

10. The electrostatic capacitance detection device of claim 1, wherein the compressor stores a blend of the oil and the refrigerant in which the refrigerant is dissolved in the oil, wherein the electrostatic capacitance detection device further comprises:

a temperature sensor configured to measure a temperature of the blend of oil and refrigerant in which refrigerant is dissolved in oil; and a control unit, in which temperature dependence of a dielectric constant of the oil and a dielectric constant of the refrigerant is stored, and wherein the control unit is configured to detect a concentration of the refrigerant or a concentration of the oil based on the temperature of the blend in which the refrigerant is dissolved in the oil, the temperature being measured by the temperature sensor, the voltage measured by the voltage detecting unit, and the temperature dependence.

11. The electrostatic capacitance detection device of claim 1, wherein, under a state in which the compressor stops a compression operation, the compressor is applied with a voltage having a frequency that is higher than a PWM control frequency during the compression operation from the inverter so that the voltage between the electrodes is detected.

12. The electrostatic capacitance detection device of claim 1, wherein the terminal disposed at the junction of an interior and exterior of the compressor is a glass terminal.

13. A power conversion apparatus, comprising:

an electrode pair;

a compressor, in which the electrode pair is placed;

a capacitor connected in series to the electrode pair via a terminal disposed at a junction of an interior and exterior of the compressor;

a voltage detecting unit configured to detect a voltage between electrodes of the electrode pair; and an inverter, which has one of power lines connected to one end of the series-connected electrode pair and capacitor, and is configured to drive the compressor.

14. An electrostatic capacitance detection device, comprising:

an electrode pair including a pair of electrodes, the electrode pair being included in a liquid container;

a capacitor connected in series to the electrode pair via a terminal disposed at a junction of an interior and exterior of the liquid container;

an inverter having a power line connected to one end of the series-connected electrode pair and capacitor, the power line being used for driving a device;

a liquid, which is stored in the liquid container, and is to be used by the device driven by the inverter; and a voltage detecting unit configured to measure a voltage between the electrode pair.

* * * * *